(12) United States Patent
Deal et al.

(10) Patent No.: US 10,219,889 B2
(45) Date of Patent: Mar. 5, 2019

(54) BALLOON EXPANDABLE URETERAL STENT

(75) Inventors: Travis Deal, Freedom, IN (US); Ray Amos, Spencer, IN (US); Mark Hera, Bloomington, IN (US); Jennifer Keeler, Hopkinton, MA (US); Jeff Smith, Poland, IN (US); Nancy Deal, legal representative, Freedom, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 262 days.

(21) Appl. No.: 13/489,159

(22) Filed: Jun. 5, 2012

(65) Prior Publication Data

US 2012/0316656 A1 Dec. 13, 2012

Related U.S. Application Data

(60) Provisional application No. 61/495,599, filed on Jun. 10, 2011.

(51) Int. Cl.
*A61F 2/04* (2013.01)
*A61M 27/00* (2006.01)

(52) U.S. Cl.
CPC ............. *A61F 2/04* (2013.01); *A61M 27/008* (2013.01); *A61F 2002/048* (2013.01)

(58) Field of Classification Search
CPC ...... A61M 31/00; A61F 2/04; A61F 2002/004
USPC .................................. 623/23.64–23.7; 604/8
See application file for complete search history.

(56) References Cited

U.S. PATENT DOCUMENTS

| | | | |
|---|---|---|---|
| 6,364,868 B1* | 4/2002 | Ikeguchi | 604/514 |
| 6,488,557 B1 | 12/2002 | Elliott et al. | |
| 6,656,146 B1* | 12/2003 | Clayman | A61M 27/008 604/544 |
| 6,685,744 B2 | 2/2004 | Gellman et al. | |
| 6,764,519 B2* | 7/2004 | Whitmore, III | A61M 27/008 623/23.64 |
| 7,445,642 B2 | 11/2008 | Amos et al. | |
| 9,339,633 B2* | 5/2016 | Tchirikov | A61M 25/02 |
| 2005/0234388 A1* | 10/2005 | Amos | A61M 27/008 604/8 |
| 2005/0240278 A1* | 10/2005 | Aliski | A61M 27/008 623/23.7 |
| 2008/0086214 A1* | 4/2008 | Hardin | A61F 2/04 623/23.7 |
| 2009/0030370 A1 | 1/2009 | Nishtala et al. | |
| 2010/0076574 A1* | 3/2010 | Gellman | A61F 2/88 623/23.66 |
| 2010/0241240 A1* | 9/2010 | Willard | A61M 27/008 623/23.66 |

(Continued)

*Primary Examiner* — Suzette J Gherbi

(57) ABSTRACT

An apparatus is provided that includes an elongate member having a distal end portion, a proximal end portion, and a medial portion that is disposed between the distal end portion and the proximal end portion. The medial portion is configured to be disposed in a ureter of a patient. The apparatus further includes an expandable member that is coupled to the elongate member. The expandable member has an expanded configuration and a collapsed configuration. The expandable member is further configured to be inserted into the ureter of the patient and configured to contact the ureter to help retain the elongate member in place within the patient.

17 Claims, 26 Drawing Sheets

(56) References Cited

U.S. PATENT DOCUMENTS

| | | | |
|---|---|---|---|
| 2010/0274231 A1* | 10/2010 | Pravong | A61B 17/22 |
| | | | 606/2.5 |
| 2012/0083899 A1* | 4/2012 | Whitmore, III | A61M 27/008 |
| | | | 623/23.66 |
| 2012/0316656 A1* | 12/2012 | Deal | A61F 2/04 |
| | | | 623/23.7 |
| 2014/0142721 A1* | 5/2014 | Robertson | A61L 31/145 |
| | | | 623/23.66 |
| 2015/0223866 A1* | 8/2015 | Buelna | A61K 31/045 |
| | | | 600/3 |

\* cited by examiner

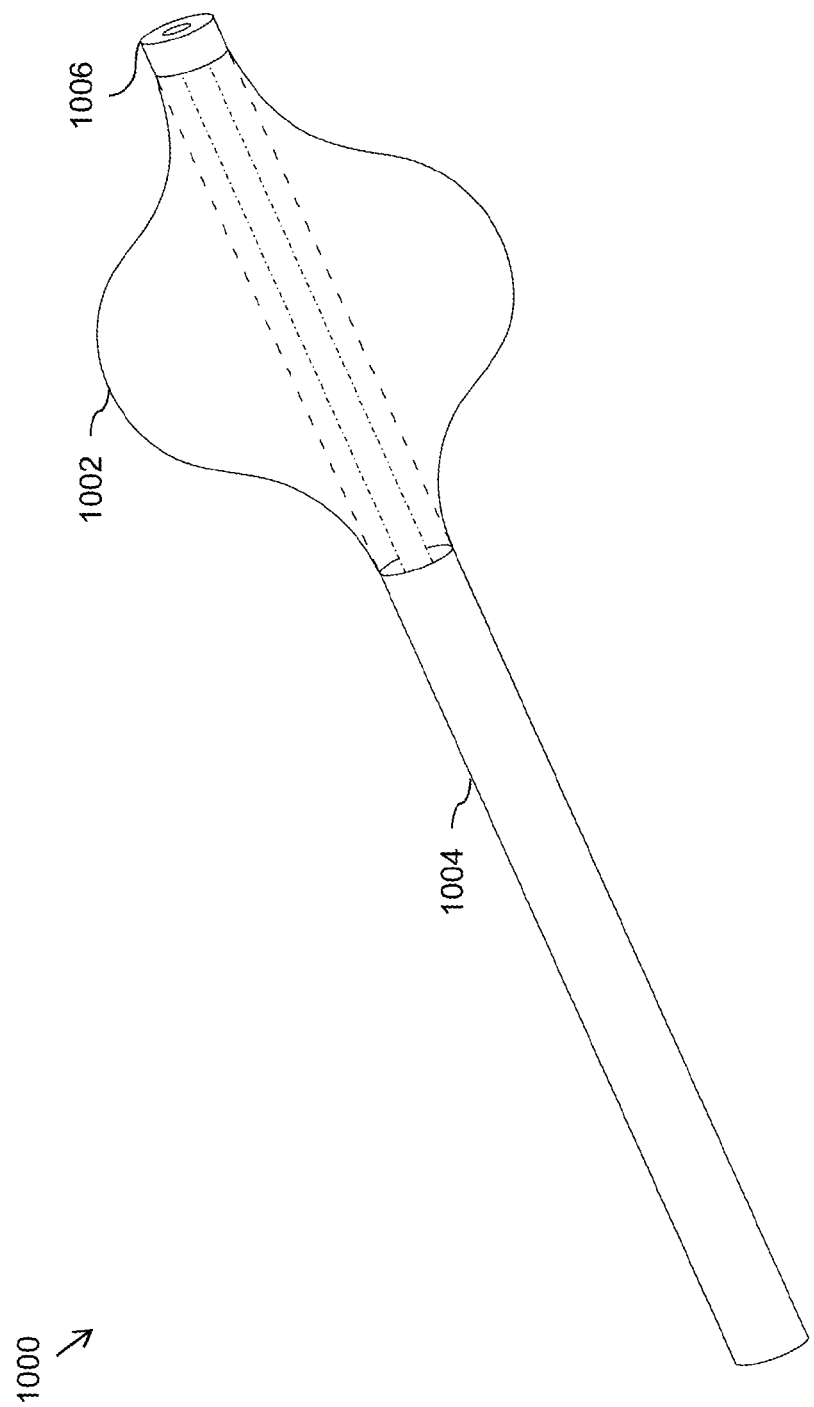

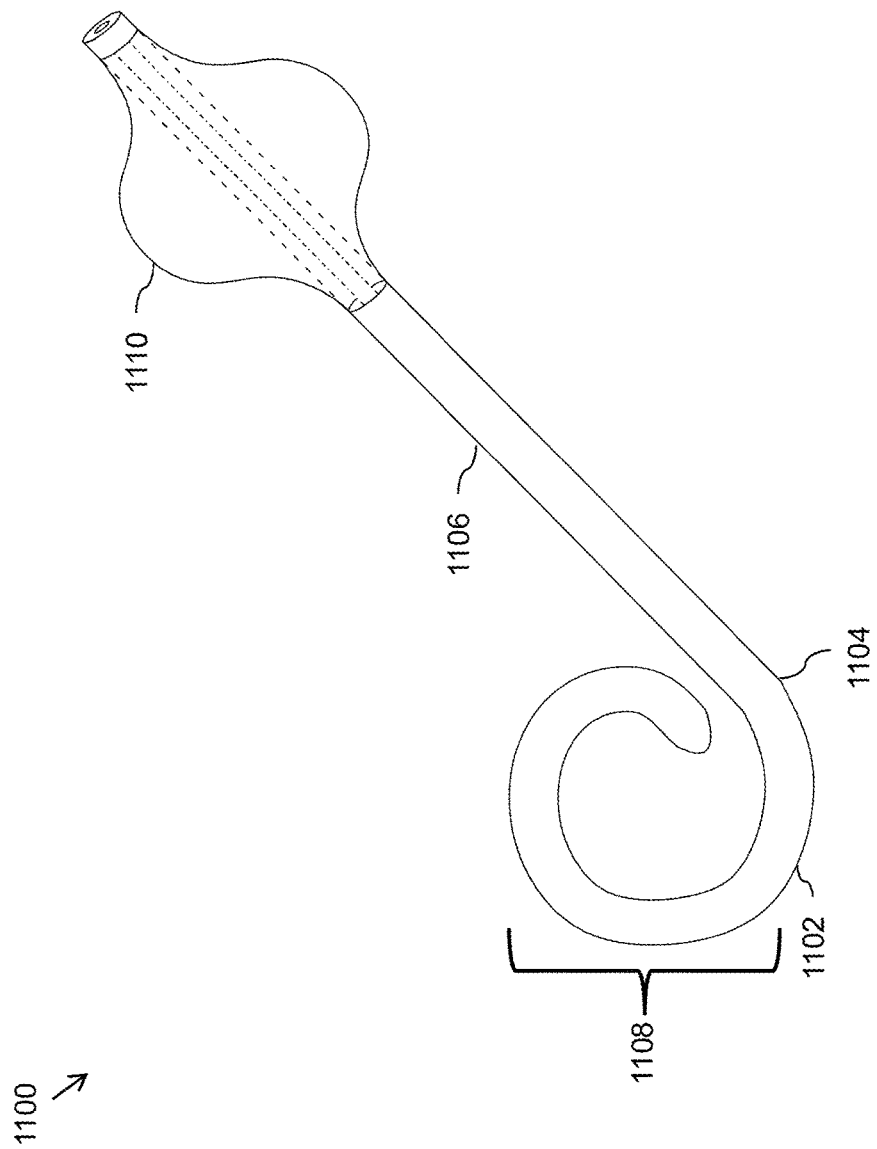

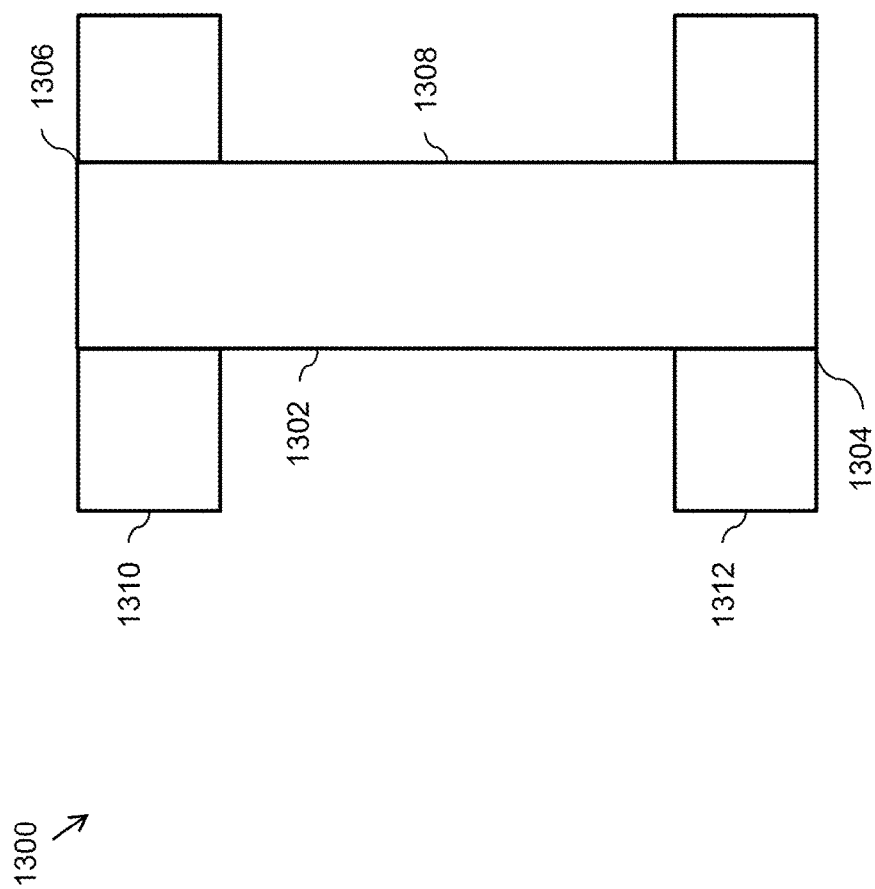

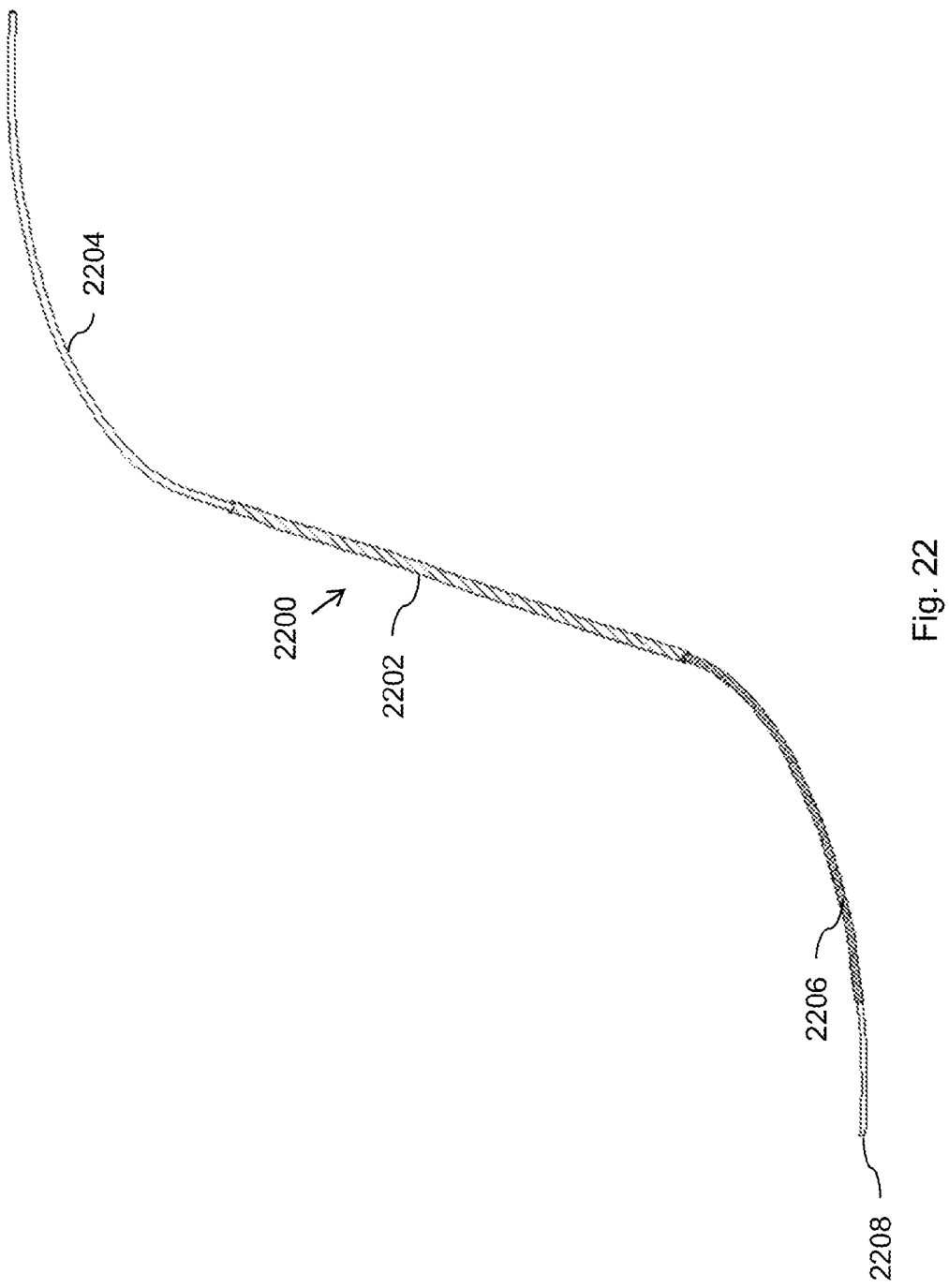

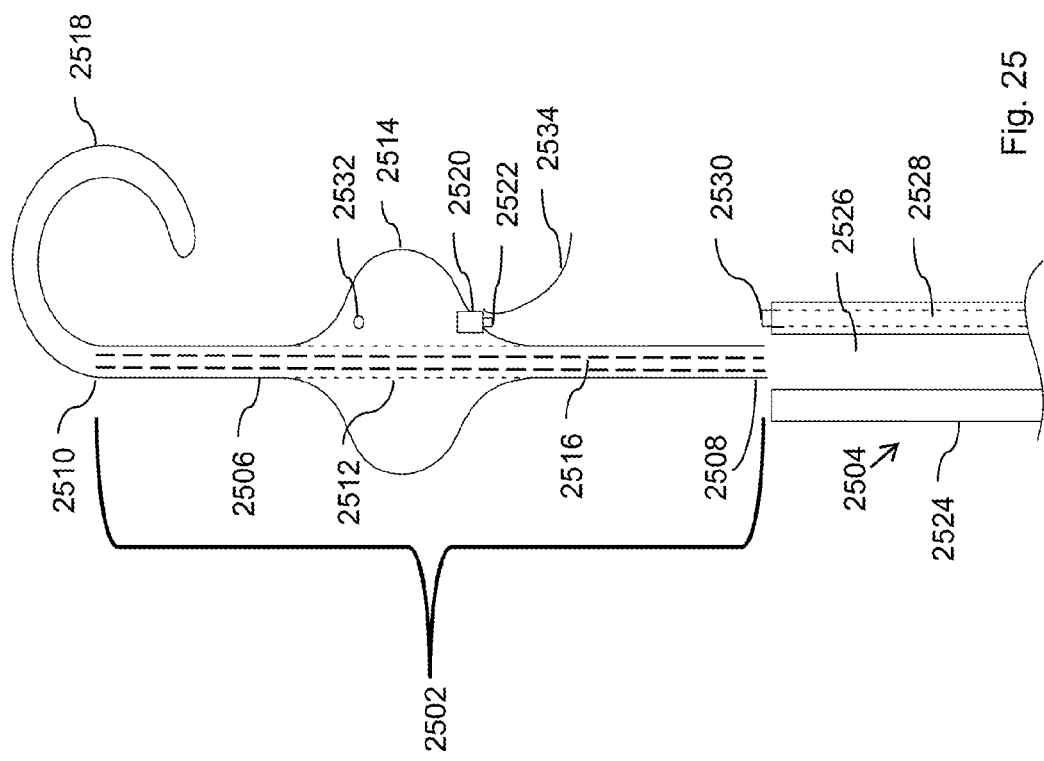

BALLOON EXPANDABLE URETERAL STENT

CROSS REFERENCE TO RELATED APPLICATION

This application is a Nonprovisional of, and claims priority to, U.S. Provisional Application No. 61/495,599, filed on Jun. 10, 2011, entitled "BALLOON EXPANDABLE STENT", which is incorporated by reference herein in its entirety.

BACKGROUND

Field

The invention generally relates to medical devices and procedures, and more particularly to implantation of a medical device into a body of a patient to ensure the patency of a ureter and minimize patient discomfort.

The invention generally relates to medical devices and procedures, and more particularly to implantation of a medical device into a body of a patient to ensure the patency of a ureter and minimize patient discomfort.

Description of the Related Art

Medical devices such as ureteral stents are used to create a pathway for urinary drainage from a kidney to a urinary bladder of a patient with ureteral obstruction or injury, or to protect the integrity of a ureter in various surgical operations. A number of clinical conditions may produce interruption in urine flow including, for example, intrinsic obstruction of the ureter due to tumor growth, stricture or stones, compression of the ureter due to extrinsic tumor growth, stone fragment impactation in the ureter following Extracorporeal Shock Wave Lithotripsy (ESWL), and ureteral procedures such as ureteroscopy and endopyelotomy. Stents may be used to treat or avoid obstructions of the ureter (such as ureteral stones or ureteral tumors) that disrupt the flow of urine from the kidney to the urinary bladder. Serious obstructions of a urinary tract may cause urine to flow back into the kidney, threatening renal function. The stent may be placed in the ureter to facilitate the flow of urine from the kidney to the urinary bladder and to enable the ureter to heal.

Ureteral stents typically are tubular in shape, terminating in two opposing ends: a kidney distal end and a urinary bladder proximal end. One or both ends of the stent may be coiled in a pigtail spiral or J-shape to prevent the upward and/or downward migration of the stent in a lumen of the ureter due to, for example, the day-to-day physical activity of the patient. The ureteral stent may reside inside the body of the patient for typically three to thirty days, but can be there for as long as one year. A kidney end coil is designed to retain the stent within a kidney or renal pelvis and to prevent the migration of the ureteral stent down the ureter. A urinary bladder end coil is positioned in the urinary bladder and is designed to prevent migration of the ureteral stent upward toward the kidney. The urinary bladder end coil may also be used to aid in retrieval and removal of the ureteral stent.

The use of coils at the kidney distal end and the urinary bladder proximal end in the ureteral stent can result in patient discomfort when the typical indwelling stent comes in contact with these regions of the patient. Typical ureteral stents, particularly the portion positioned in the urinary bladder, may produce adverse effects, including hemorrhage, a continual urge to urinate, and flank pain accompanying reflux of urine back up the ureter due to retrograde pressure when voiding.

Flank pain may be caused from typical ureteral stents during urinary voiding. On the initiation of voiding the urinary bladder, wall muscles contract causing the pressure inside the urinary bladder to rise. Since a typical indwelling ureteral stent holds a ureteral orifice open, this pressure can cause urine to be transmitted to the kidney causing the patient to experience pain. Attempts to mitigate some of these problems associated with ureteral stents include administering systemic pharmaceuticals such as anti-spasmodic drugs that may present additional undesirable side effects. In general, known ureteral stents may cause or contribute to significant patient discomfort and serious medical problems.

Existing solutions to reduce the patient discomfort have focused on reducing the mass in the urinary bladder end coil of the ureteral stent, or using a softer material in place of the coils.

In accordance with the foregoing, there is a need for devices and methods for providing an improved urinary stent that ensures the patency of a ureter of a patient and minimizes patient discomfort in the kidney and bladder areas.

SUMMARY

An apparatus for ensuring the patency of a ureter of a patient is provided. The apparatus includes an elongate member having a distal end portion, a proximal end portion, and a medial portion that is disposed between the distal end portion and the proximal end portion. The medial portion is configured to be disposed in a ureter of a patient. The apparatus further includes an expandable member that is coupled to the elongate member. The expandable member has an expanded configuration and a collapsed configuration. The expandable member is further configured to be inserted into the ureter of the patient and configured to contact the ureter to help retain the elongate member in place within the patient.

BRIEF DESCRIPTION OF THE FIGURES

The invention and the following detailed description of certain embodiments thereof may be understood by reference to the following figures:

FIG. 10 is a perspective view of a medical device in an expanded configuration, in accordance with an embodiment of the invention;

FIG. 11 is a perspective view of a medical device in an expanded configuration, in accordance with another embodiment of the invention;

FIG. 13 is a schematic diagram of a medical device to be delivered into a patient's body, in accordance with an embodiment of the invention;

FIG. 22 illustrates a perspective view of a medical device in a pre-deployed or collapsed configuration, in accordance with an embodiment of the invention;

FIG. 25 is a front view of a medical device and an insertion device, in accordance with an embodiment of the invention.

DETAILED DESCRIPTION

Figure 1:
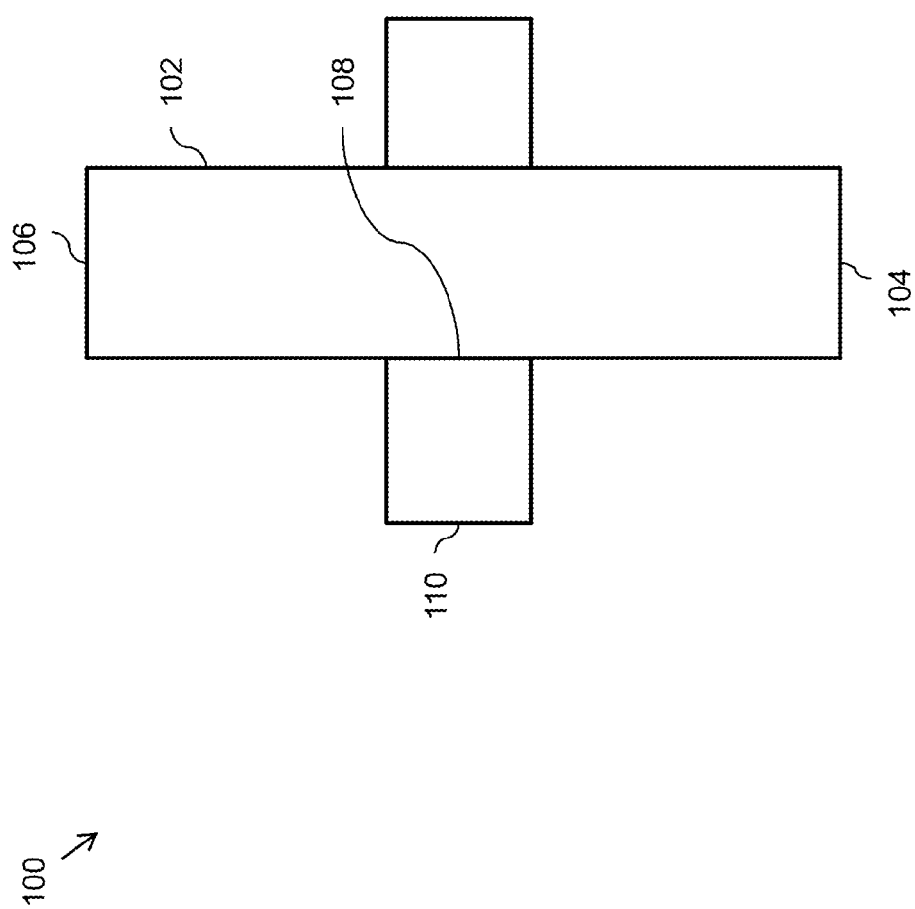
FIG. 1 is a schematic diagram of a medical device to be delivered into a body of a patient, in accordance with an embodiment of the invention.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

The terms proximal, distal, and medial described in relation to various devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like, who may perform the procedure of delivery and placement of a medical device into a body of a patient as described in the present invention. The patient may be a human female, a human male, or any other mammal. The term proximal refers to an area that is closest to the operator. The term distal refers to an area that is farthest from the operator. The term medial refers to an area that pertains to middle, in or toward the middle, or nearer the middle of a device or an apparatus or a component.

The present invention relates to devices and methods for implantation of a medical device into a body of a patient to ensure the patency of a ureter of the patient and minimize patient discomfort. Medical devices such as ureteral stents create a pathway for urinary drainage from a kidney to a urinary bladder of the patient with ureteral obstruction or injury, or to protect the integrity of the ureter in various surgical operations. A number of biomaterials are available for construction of a ureteral stent. In some embodiments, the biomaterials exhibit at least some of the following characteristics: high tensile strength, high retention coil strength, excellent biocompatibility and biodurability, excellent radiopacity or fluoroscopic visibility, availability in varying durometers, and low resistance to passage. In some embodiments, the ureteral stent may be constructed from shape memory tubing, such as, but not limited to, PERCU-FLEX® (Boston Scientific Corporation, Natick, Mass.), C-FLEX® (Xomed-Trease, Inc.), FLEXIMA™, or other polymer material including polytetrafluoroethylene (PTFE), silicone polyurethane, polyurethane plastics, polyethylene plastics, and thermoplastics for example.

FIG. 1 is a schematic diagram of a medical device 100 to be delivered into a patient's body, in accordance with an embodiment of the invention. The medical device 100 may be a ureteral stent that is utilized to ensure the patency of a ureter of the patient and minimize patient discomfort. The medical device 100 includes an elongate member 102 having a proximal end portion 104, a distal end portion 106, and a medial portion 108. The proximal end portion 104 is an end of the elongate member 102 that is closest to an operator handling the medical device 100. Likewise, the distal end portion 106 is an end of the elongate member 102 that is farthest from the operator handling the medical device 100. The medial portion 108 is disposed between the distal end portion 106 and the proximal end portion 104 of the elongate member 102. In some embodiments, the medial portion 108 is an area that pertains to middle, in or toward the middle, or nearer the middle of the elongate member 102.

The medical device 100 may further include an expandable member 110 that may be coupled to the elongate member 102. In some embodiments, the expandable member 110 may be a balloon that may surround at least a portion of an external surface of the elongate member 102. In other embodiments, the expandable member 110 may be any other expandable material that is configured to expand and to collapse. Referring to FIG. 1, the expandable member 110 is positioned at the medial portion 108 of the elongate member 102. The operator may deliver the medical device 100 into the body of the patient such that the expandable member 110 is disposed within a ureter of the patient. In some embodiments, the expandable member 110 may be placed in a collapsed configuration to allow insertion of the medical device 100 into the body of the patient. The collapsed configuration refers to a deflated condition of the expandable member 110 for ease of passage through a urethra of the patient during insertion of the medical device 100 into the body of the patient. Further, the expandable member 110 is configured to contact the ureter to help retain the elongate member 102 in place within the patient. In some embodiments, the expandable member 110 may be disposed in an expanded configuration to contact the ureter of the patient. The expanded configuration refers to an expanded or inflated condition of the expandable member 110 to help retain the elongate member 102 in the ureter. As shown in FIG. 1, the expandable member 110 extends along both the longitudinal edges of the elongate member 102. In other embodiments, the expandable member 110 only extends along one longitudinal edge or along a portion of the elongate member 102.

In some embodiments, the expandable member 110 may be constructed from a material with similar properties to the elongate member 102. In some other embodiments, the expandable member 110 may be constructed from a material with different properties than that in the elongate member 102.

In some embodiments, the expandable member 110 may be integrally or unitarily formed with the elongate member 102. In other embodiments, the expandable member 110 may be coupled, such as fixedly coupled or removably coupled, to the elongate member 102. The size and shape of the elongate member 102 and the expandable member 110 as illustrated in FIG. 1 are merely exemplary, and various other shapes and sizes are possible without limiting the spirit and scope of the invention.

Figure 2:
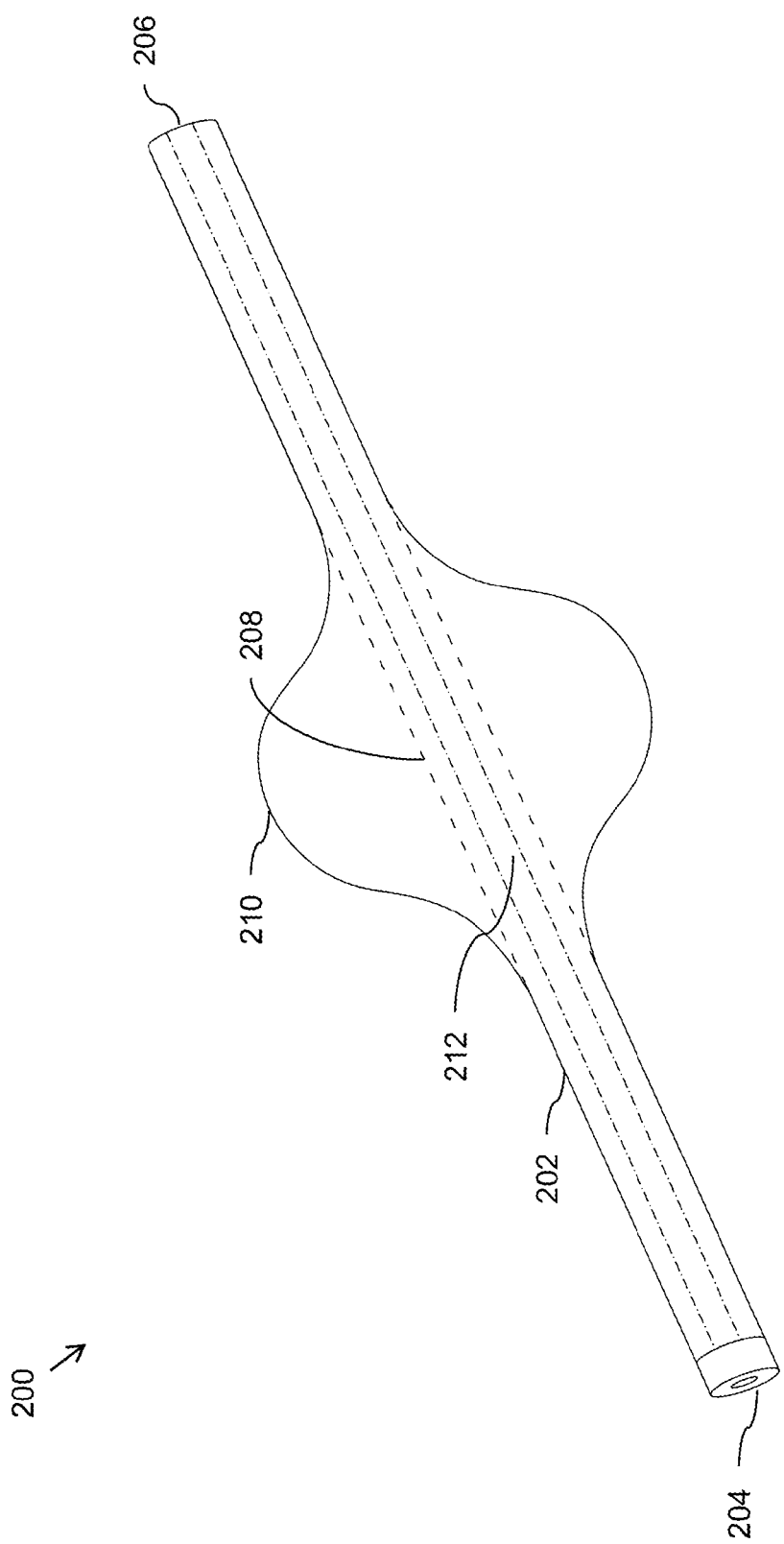
FIG. 2 is a perspective view of a medical device in an expanded configuration, in accordance with an embodiment of the invention.

FIG. 2 is a perspective view of a medical device 200 in an expanded configuration, in accordance with an embodiment of the invention. The medical device 200 may be a ureteral stent that includes an elongate member 202 having a proximal end portion 204, a distal end portion 206, and a medial portion 208 that may be disposed at a medial location of the elongate member 202 between the distal end portion 206 and the proximal end portion 204. The elongate member 202 extends longitudinally between the distal end portion 206 and the proximal end portion 204.

The medical device 200 may further include an expandable member 210 that may be coupled to the elongate member 202. Similar to FIG. 1, the expandable member 210 is positioned at the medial portion 208 of the elongate member 202. In some embodiments, the expandable member 210 may surround the medial portion 208 of the elongate member 202. The operator may deliver the medical device 200 in the body of the patient such that the expandable member 210 is configured to be inserted into the ureter of the patient through the urethra of the patient. In some embodiments, the expandable member 210 may be disposed or placed in the collapsed configuration to allow insertion into the body of the patient. The collapsed configuration refers to a deflation condition of the expandable member 210 for ease of passage through the urethra of the patient during insertion of the medical device 200 into the body of the patient. Further, the expandable member 210 is configured to contact the ureter to help retain the elongate member 202 in place within the patient. In some embodiments, the expandable member 210 may be placed in or disposed in the expanded configuration to contact the ureter of the patient. The expanded configuration refers to an inflation condition of the expandable member 210 to help retain the elongate member 202 in the ureter. As shown in FIG. 2, the expandable member 210 is in the expanded configuration and surrounds at least a portion of the elongate member 202.

The elongate member 202 defines a lumen 212 that extends between the proximal end portion 204 and the distal end portion 206 along a longitudinal axis of the elongate member 202. In some embodiments, the lumen 212 of the elongate member 202 may be disposed through a center of the expandable member 210 and/or may permit drainage of urine from a kidney of the patient directly into a urinary bladder of the patient. The size of the lumen 212 is sufficient to facilitate in the ease of flushing of stone fragments with urine drainage from the kidney into the urinary bladder of the patient. For example, the size of the lumen may be at least one-half centimeter.

In some embodiments, one or both ends of a medical device may be coiled in a spiral shape or J-shape or substantially helical shape to further prevent the upward and/or downward migration of the medical device in the ureter due to, for example, the day-to-day physical activity of the patient. A distal retention device in a kidney portion of the patient may help retain the medical device within a renal pelvis and prevent medical device migration down the ureter. Likewise, a proximal retention device in a urinary bladder portion of the patient may help prevent medical device migration upward toward the kidney. In other embodiments, one or both ends of the medical device may include one or more expandable members similar to the expandable member 110 or the expandable member 210.

Figure 3:
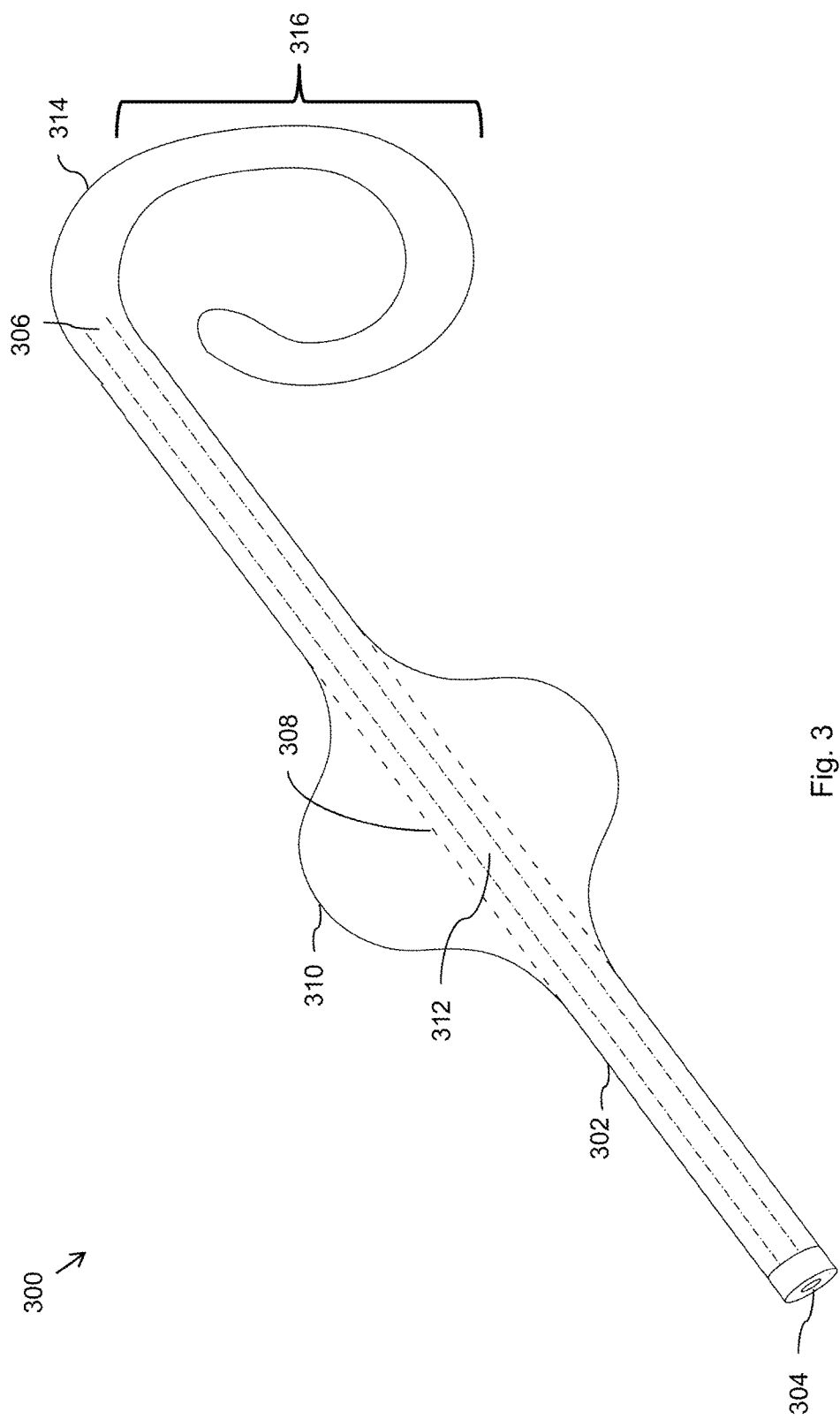
FIG. 3 is a perspective view of a medical device in an expanded configuration, in accordance with another embodiment of the invention.

FIG. 3 is a perspective view of a medical device 300 in an expanded configuration, in accordance with another embodiment of the invention. The medical device 300 may be a ureteral stent that includes an elongate member 302 having a proximal end portion 304, a distal end portion 306, and a medial portion 308 that may be disposed at a medial location of the elongate member 302 between the distal end portion 306 and the proximal end portion 304. The elongate member 302 extends longitudinally between the distal end portion 306 and the proximal end portion 204. The medical device 300 may further include an expandable member 310 that may be coupled to the elongate member 302. Similar to FIGS. 1 and 2, the expandable member 310 is positioned at the medial portion 308 of the elongate member 302. The elongate member 302 defines a lumen 312 that extends between the proximal end portion 304 and the distal end portion 306 along the longitude of the elongate member 302.

In this embodiment, the medical device 300 and its functionalities are similar to the medical device 200 and its functionalities as described in conjunction with FIG. 2, except that a distal retention device 314 is disposed proximate to the distal end portion 306 of the elongate member 302 in FIG. 3. The distal retention device 314 is formed by bending a portion 316 that is proximate to the distal end portion 306 of the elongate member 302 into a planar or a substantially planar spiral configuration as depicted in FIG. 3. The bending helps to retain the distal portion 316 or the distal end portion 306 of the medical device 300 in a renal pelvis of a kidney of the patient. In some embodiments, the expandable member 310 and the distal retention device 314 help maintain the medical device 300 in place within the body of the patient.

The size and shape of the distal retention device 314 as illustrated in FIG. 3 are merely exemplary, and various other shapes and sizes are possible without limiting the spirit and scope of the invention.

Figure 4:
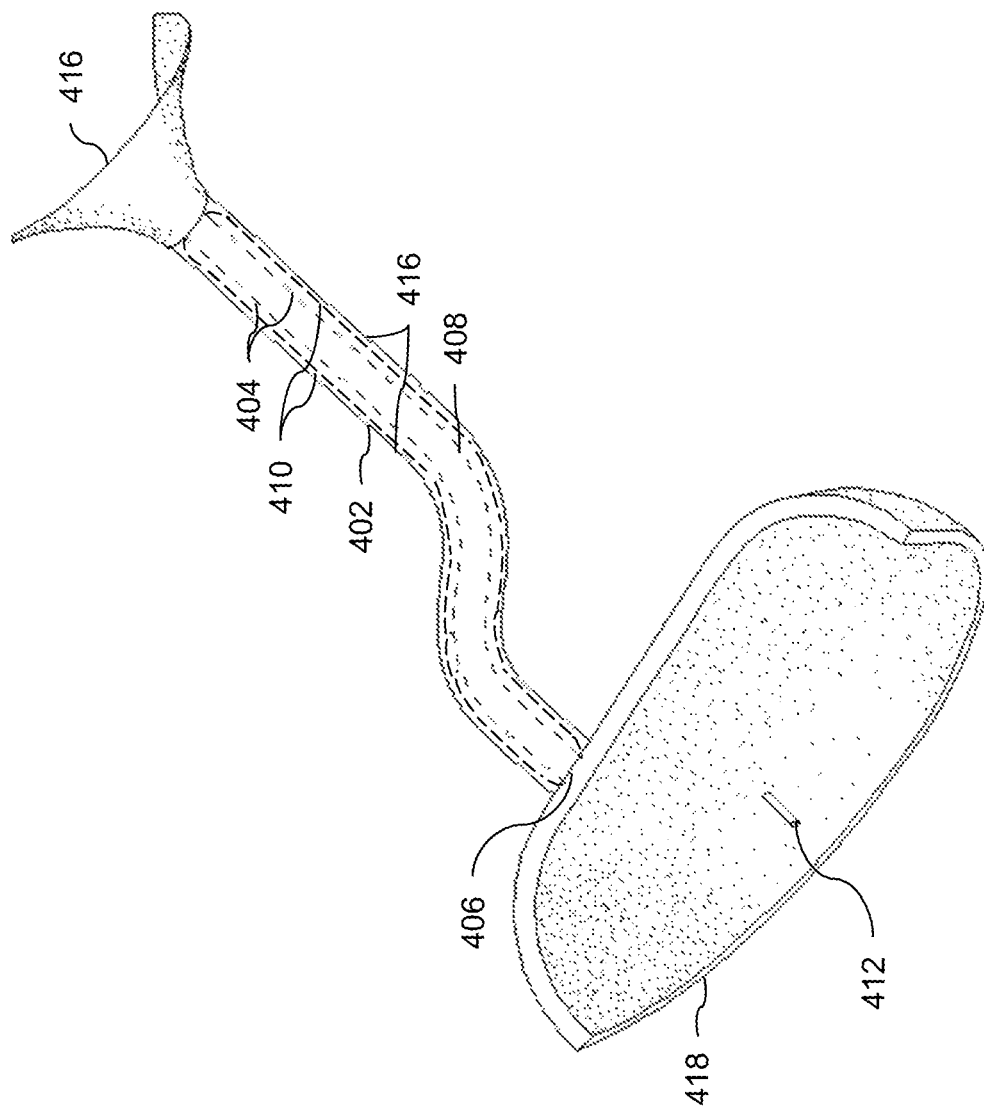
FIG. 4 schematically illustrates a medical device deployed in a ureter of a patient, in accordance with an embodiment of the invention.

FIG. 4 is a schematic illustration of a medical device deployed in a ureter 402 of a patient, in accordance with an embodiment of the invention. The medical device may be a ureteral stent that is utilized to ensure the patency of the ureter 402 of the patient and minimize patient discomfort. The medical device may include an elongate member 404 (illustrated in dashed lines in FIG. 4) having a proximal end portion 406, a distal end portion (not illustrated in FIG. 4), and a medial portion 408 that extends between the distal end portion and the proximal end portion 406.

The medical device may further include an expandable member 410 (illustrated in long dashed lines in FIG. 4) such as a balloon that may be coupled to the elongate member 404 of the medical device. The expandable member 410 may be inserted through a urethral orifice 412 of the patient in the collapsed configuration. The collapsed configuration facilitates in the ease of passage through the urethral orifice 412. In some embodiments, the diameter of the expandable member 410 is provided such that the expandable member 410 may easily pass through the urethral orifice 412 of the patient during the collapsed configuration. In other embodiments, the diameter of the expandable member 410 is provided such that, during insertion in the collapsed configuration, the expandable member 410 may easily pass through an Ureteropelvic junction (UPJ) that is a junction between the ureter 402 and a renal pelvis of a kidney of the patient. Once the medical device is inserted into a body of the patient, the expandable member 410 is disposed in an expanded configuration as illustrated in FIG. 4. In the expanded configuration, the expandable member 410 is configured to contact the ureter 402 to help retain the medical device in place within the patient. The expandable member 410 may be inflated with a fluid, such as, but not limited to, liquid, semi-liquid, gel, gas, or other biocompatible fluid. In some embodiments, a medium such as liquid saline is introduced into the expandable member 410 to inflate the expandable member 410 to a diameter that is sufficient to help retain the medical device in the ureter 402. The diameter may be of any size sufficient to help retain the medical device within the ureter or other portion of the body.

In some embodiments, the expandable member 410 may be positioned entirely in the ureter 402. In other embodiments, the expandable member 410 may be positioned in at least a portion of the ureter 402. The expandable member 410 is expanded to an extent that the inflated expandable member 410 contacts walls 416 of the ureter 402. In some embodiments, the force exerted by the expandable member against the walls 416 of the ureter 402 results in holding the medical device in place within the body of the patient.

In some embodiments, the proximal end portion 406 of the elongate member 404 may extend into a urinary bladder 418 of the patient. In other embodiments, the distal end portion of the elongate member 404 may extend into the renal pelvis of the patient. The expandable member 410 surrounds an external surface of the medial portion 408 of the elongate member 404.

Figure 5:
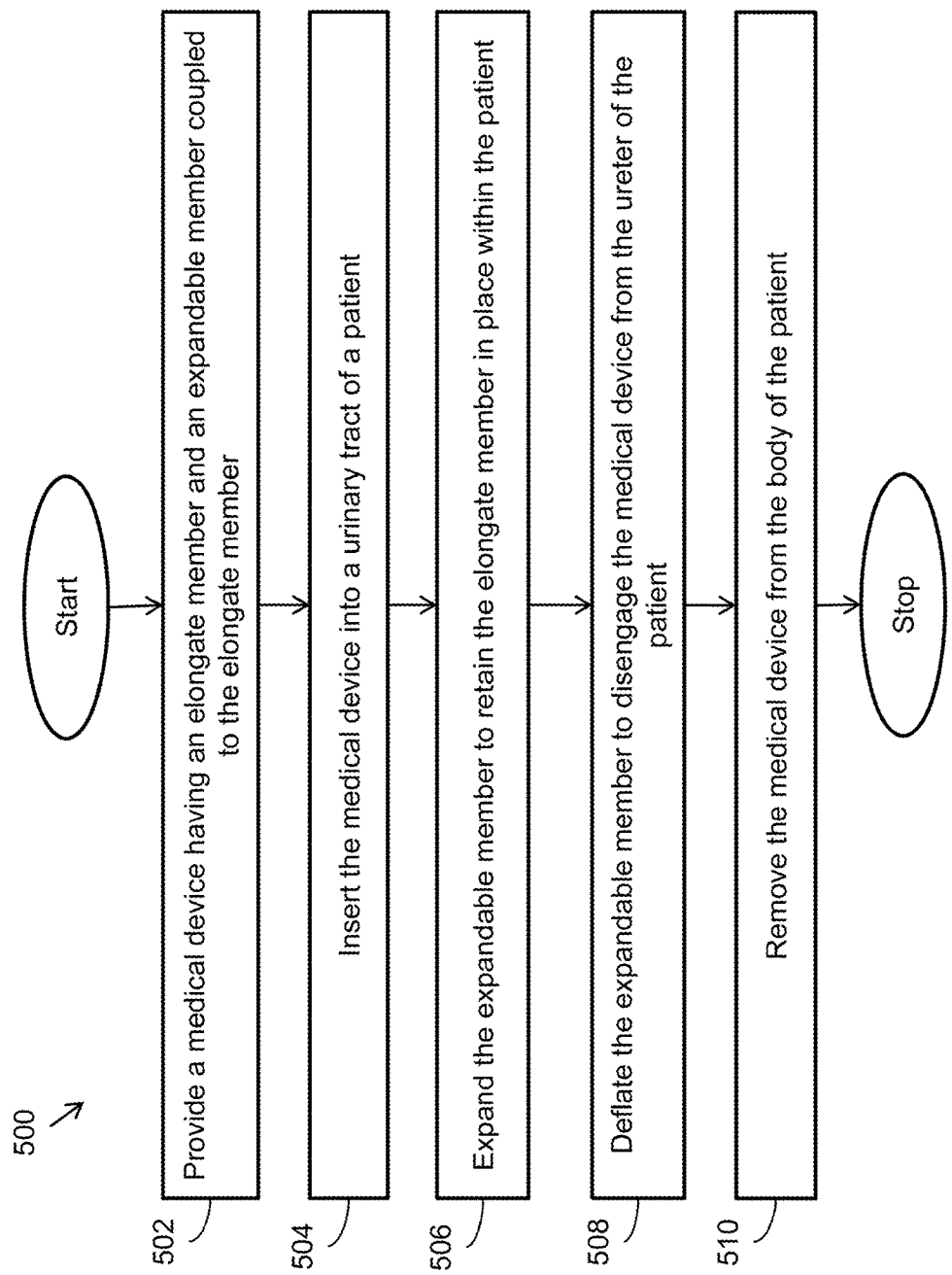
FIG. 5 is a flowchart illustrating a method of implantation and removal of a medical device, in accordance with an embodiment of the invention.

FIG. 5 is a flowchart illustrating a method 500 of implantation and removal of a medical device, in accordance with an embodiment of the invention. The medical device may be any of the medical devices 100, 200, 300, and 402. The method 500 includes providing the medical device having an elongate member and an expandable member coupled to the elongate member at step 502. The elongate member may have a proximal end portion, a distal end portion, and a medial portion that is disposed between the distal end portion and the proximal end portion of the elongate member. In some embodiments, the expandable member may be a balloon that may surround at least a portion of an external surface of the elongate member. The expandable member may be positioned at the medial portion of the elongate member.

At step 504, an operator inserts the medical device into a urinary tract of the patient. The operator may deliver the medical device in the body of the patient such that the expandable member and the elongate member are configured to be inserted into a ureter of the patient. The expandable member may be inserted through a urethral orifice of the patient in the collapsed configuration. The collapsed configuration facilitates in the ease of passage through the urethral orifice. In some embodiments, the diameter of the expandable member is provided such that the expandable member may easily pass through the urethral orifice of the patient. In some embodiments, the diameter of the expandable member is provided such that, during insertion in the collapsed configuration, the expandable member may easily pass through a UPJ of the patient.

There are two conventional techniques of placing the medical devices. In the first technique, a guidewire of sufficient stiffness and maneuverability is inserted into the ureter under endoscopic guidance. Once the guidewire has been inserted into the body (for example, passed into the kidney, the medical device is introduced to the ureter over the guidewire using an insertion device such as a pusher catheter acting on a proximal end of the medical device. The second technique omits the prior step of placing the guidewire and may be used where no large obstruction is present. In this technique, the guidewire is inserted through the medical device only until it is flush with or within the tip of the medical device. The pusher catheter is inserted behind the medical device on the guidewire and is locked to the guidewire with a locking hub (e.g., SPEED-LOK® product available from Boston Scientific Corp.). The assembly is then pushed by the pusher catheter acting on the proximal end of the medical device to enter the ureter. In an embodiment, the medical device is engaged by passing the pusher catheter through a urinary bladder of the patient. In another embodiment, the medical device is engaged by inserting at least a portion of the pusher catheter into the ureter. The technique of placing the medical device using the pusher catheter is explained in detail in conjunction with FIGS. 22 and 23. The medical devices such as ureteral stents may be introduced in the body either cystoscopically in a retrograde fashion, or percutaneously in an antigrade fashion, using for example, an adaptation of a Seldinger technique.

Thereafter, at step 506, a valve coupled to the elongate member or the expandable member is used to expand or inflate the expandable member to retain the elongate member in place within the patient. In some embodiments, the expandable member is configured in an expanded configuration so as to contact the ureter to help retain the elongate member in place within the patient. The expanded configuration refers to an inflation condition of the expandable member to help retain the elongate member in the ureter. The expandable member is expanded to an extent that the inflated expandable member contacts walls of the ureter. The force exerted by the expandable member against the walls of the ureter results in holding the medical device in place within the body of the patient.

The expandable member may be inflated after insertion into the body of the patient with a fluid, such as, but not limited to, liquid, semi-liquid, gel, gas, or other biocompatible fluid. In some embodiments, a medium such as liquid saline is introduced into the expandable member to inflate the expandable member to a suitable diameter to help retain the medical device in the ureter.

In some embodiments, one or both ends of the medical device may be coiled in a spiral shape or J-shape or substantially helical shape to further prevent the upward and/or downward migration of the medical device in the ureter due to, for example, the day-to-day physical activity of the patient. A distal retention device in a renal pelvis of the patient may help retain the medical device within the renal pelvis and prevent medical device migration down the ureter. Likewise, a proximal retention device in a urinary bladder of the patient may help prevent medical device migration upward toward the kidney. In other embodiments, one or both ends of the medical device may include one or more expandable members similar to the expandable member positioned at the medial portion of the elongate member.

Further, at step 508, the operator deflates the expandable member to disengage the medical device from the ureter of the patient. In some embodiments, the operator may deflate the expandable member using a retrieval suture that is coupled to the elongate member and configured to place the expandable member in the collapsed configuration. In this case, the retrieval suture may remove a plug in the expandable member to deflate the expandable member. In other embodiments, a needle device or a syringe may be used to deflate the expandable member. In another embodiment, the valve, which is used to inflate the expandable member, may be used to deflate the expandable member. In yet another embodiment, a laser-type device may be inserted within the body of the patient to provide energy to the expandable member to deflate the expandable member. Using any of these devices, the operator may deflate the expandable member such that the diameter of the expandable member is restored to substantially the same diameter as the diameter of the medial portion of the elongate member.

The ureteral stent may reside inside the body of the patient for typically three to thirty days, but can be there for as long as one year. Finally, at step 510, the operator removes the medical device from the body of the patient. In some embodiments, the retrieval suture may be disposed proximate to the proximal end portion of the medical device for retrieval of the medical device from the urinary tract of the patient. In other embodiments, the proximal retention device may facilitate the operator in the removal of the medical device.

Figure 6:
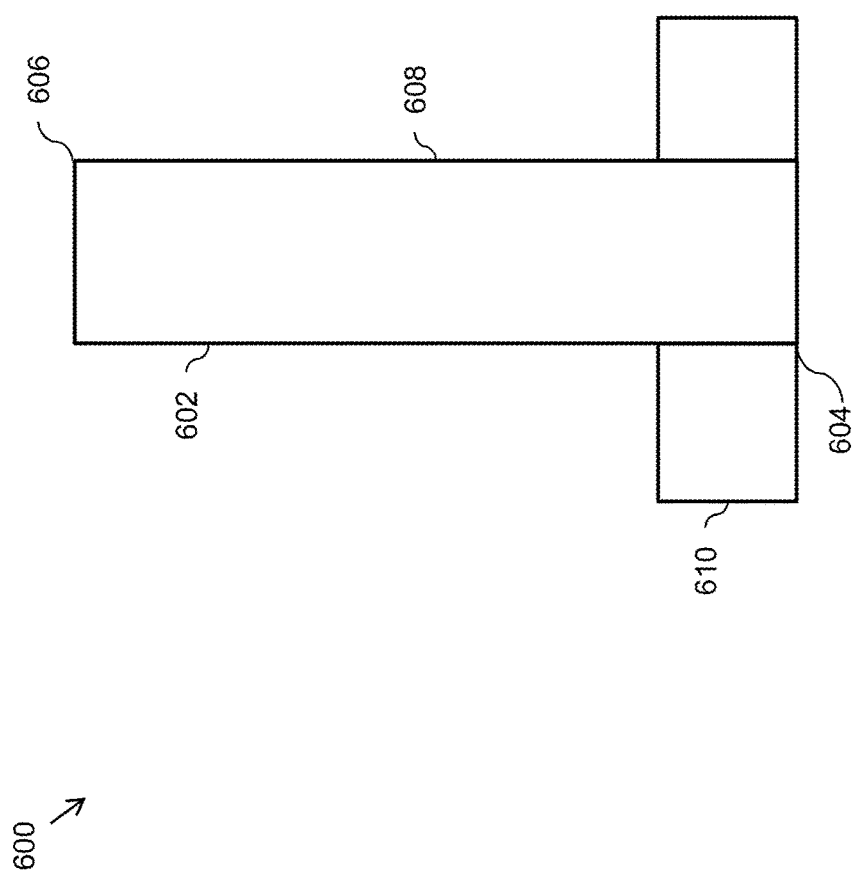
FIG. 6 is a schematic diagram of a medical device to be delivered into a patient's body, in accordance with an embodiment of the invention.

FIG. 6 is a schematic diagram of a medical device 600 to be delivered into a patient's body, in accordance with an embodiment of the invention. The medical device 600 may be a ureteral stent similar to the medical device 100 explained above in conjunction with FIG. 1. The medical device 600 includes an elongate member 602 having a proximal end portion 604, a distal end portion 606, and a medial portion 608 that is disposed between the distal end portion 606 and the proximal end portion 604 of the elongate member 602.

The medical device 600 may further include an expandable member 610 that may be coupled to the elongate member 602. In some embodiments, the expandable member 610 may be a balloon that may surround at least a portion of an external surface of the elongate member 602. Referring to FIG. 6, the expandable member 610 is disposed at the proximal end portion 604 of the elongate member 602. The operator may deliver the medical device 600 in the body of the patient such that the expandable member 610 is configured to be inserted into a urinary bladder of the patient. The rest of the functionalities, arrangements, and implantation procedures of the medical device 600 and its sub-elements are the same as that of the medical device 100.

Figure 7:
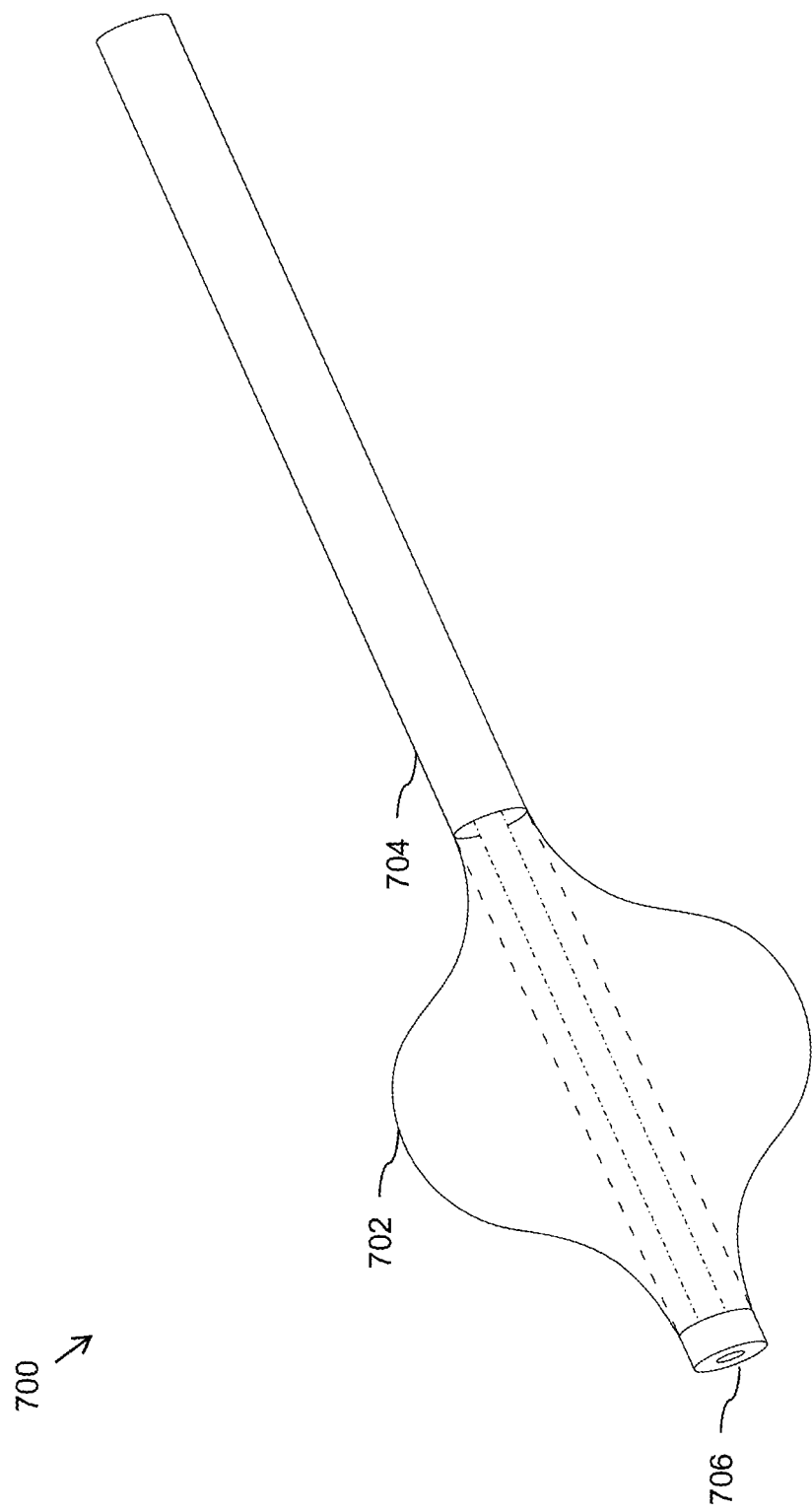
FIG. 7 is a perspective view of a medical device in an expanded configuration, in accordance with an embodiment of the invention.

FIG. 7 is a perspective view of a medical device 700 in an expanded configuration, in accordance with an embodiment of the invention. The medical device 700 includes an expandable member 702, in the expanded configuration, surrounding at least a portion of an elongate member 704 of the medical device 700. Referring to FIG. 7, the expandable member 702 is disposed at a proximal end portion 706 of the elongate member 704. The operator may deliver the medical device 700 in the body of the patient such that the expandable member 702 is configured to be inserted into a urinary bladder of the patient. The rest of the functionalities, arrangements, and implantation procedures of the medical device 700 and its sub-elements are the same as that of the medical device 200.

Figure 8:
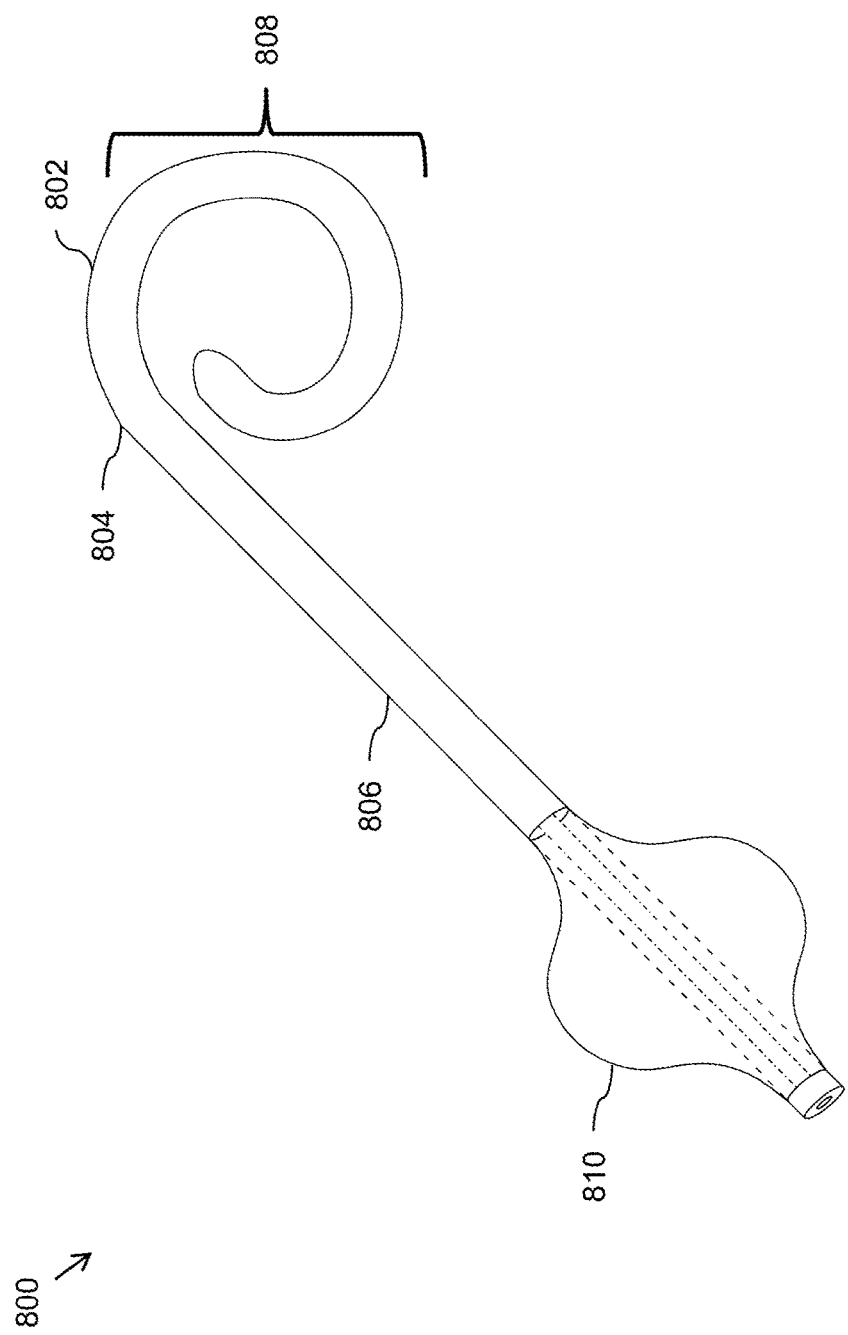
FIG. 8 is a perspective view of a medical device in an expanded configuration, in accordance with another embodiment of the invention.

FIG. 8 is a perspective view of a medical device 800 in an expanded configuration, in accordance with another embodiment of the invention. In this embodiment, the medical device 800 and its functionalities are similar to the medical device 700 and its functionalities as described in conjunction with FIG. 7, except that a distal retention device 802 is disposed proximate to a distal end portion 804 of an elongate member 806 of the medical device 800 in FIG. 8. The distal retention device 802 is formed by bending a portion 808 that is proximate to the distal end portion 804 of the elongate member 806 into a planar or a substantially planar spiral configuration as depicted in FIG. 8. The bending helps to retain the distal portion 808 or the distal end portion 804 of the medical device 800 in a renal pelvis of a kidney of the patient. In some embodiments, an expandable member 810, coupled to the elongate member 806, and the distal retention device 802 maintain the medical device 800 in situ.

The size and shape of the distal retention device 802 as illustrated in FIG. 8 are merely exemplary, and various other shapes and sizes are possible without limiting the spirit and scope of the invention.

Figure 9:
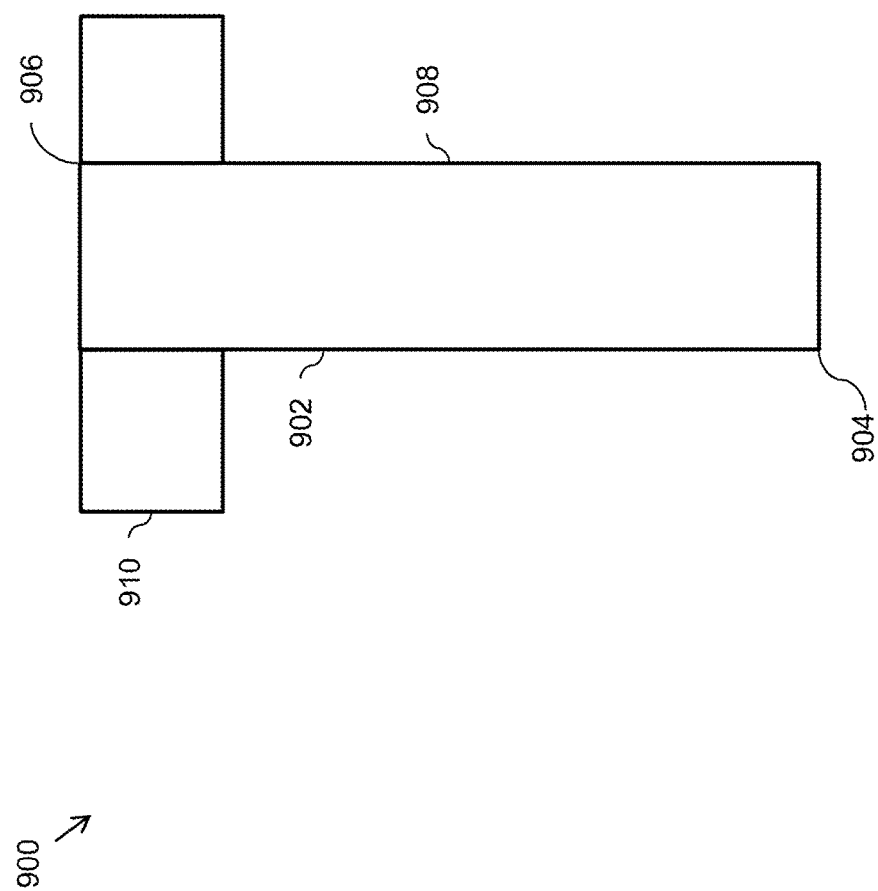
FIG. 9 is a schematic diagram of a medical device to be delivered into a patient's body, in accordance with an embodiment of the invention.

FIG. 9 is a schematic diagram of a medical device 900 to be delivered into a patient's body, in accordance with an embodiment of the invention. The medical device 900 may be a ureteral stent similar to the medical device 100 explained above in conjunction with FIG. 1. The medical device 900 includes an elongate member 902 having a proximal end portion 904, a distal end portion 906, and a medial portion 908 that is disposed between the distal end portion 906 and the proximal end portion 904 of the elongate member 902.

The medical device 900 may further include an expandable member 910 that may be coupled to the elongate member 902. In some embodiments, the expandable member 910 may be a balloon that may surround at least a portion of an external surface of the elongate member 902. Referring to FIG. 9, the expandable member 910 is disposed at the distal end portion 906 of the elongate member 902. The operator may deliver the medical device 900 in the body of the patient such that the expandable member 910 is configured to be inserted into a kidney of the patient. The rest of the functionalities, arrangements, and implantation procedures of the medical device 900 and its sub-elements are the same as that of the medical device 100.

FIG. 10 is a perspective view of a medical device 1000 in an expanded configuration, in accordance with an embodiment of the invention. The medical device 1000 includes an expandable member 1002, in the expanded configuration, surrounding at least a portion of an elongate member 1004 of the medical device 1000. Referring to FIG. 10, the expandable member 1002 is disposed at a distal end portion 1006 of the elongate member 1004. The operator may deliver the medical device 1000 into the body of the patient such that the expandable member 1002 is configured to be inserted into a renal pelvis of a kidney of the patient. The rest of the functionalities, arrangements, and implantation procedures of the medical device 1000 and its sub-elements are the same as that of the medical device 200.

FIG. 11 is a perspective view of a medical device 1100 in an expanded configuration, in accordance with another embodiment of the invention. In this embodiment, the medical device 1100 and its functionalities are similar to the medical device 1000 and its functionalities as described in conjunction with FIG. 10, except that a proximal retention device 1102 is disposed proximate to a proximal end portion 1104 of an elongate member 1106 of the medical device 1100 in FIG. 11. The proximal retention device 1102 is formed by bending a portion 1108 that is proximate to the proximal end portion 1104 of the elongate member 1106 into a planar or a substantially planar spiral configuration as depicted in FIG. 11. The bending helps to retain the proximal portion 1108 or the proximal end portion 1104 of the medical device 1100 in a renal pelvis of a kidney of the patient. In some embodiments, an expandable member 1110, coupled to the elongate member 1106, and the proximal retention device 1102 maintain the medical device 1100 in situ.

The size and shape of the proximal retention device 1102 as illustrated in FIG. 11 are merely exemplary, and various other shapes and sizes are possible without limiting the spirit and scope of the invention.

Figure 12B:
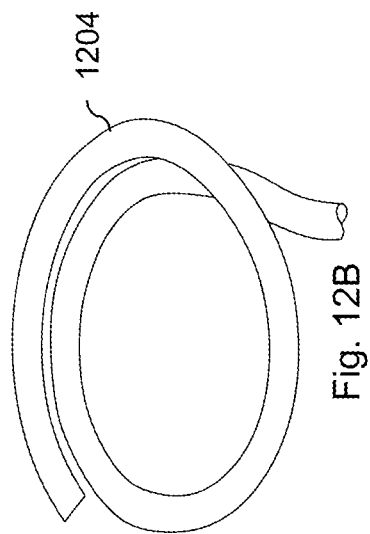
FIGS. 12A-12C depict enlarged views of various embodiments of a retention device, in accordance with an embodiment of the invention.
Figure 12A:
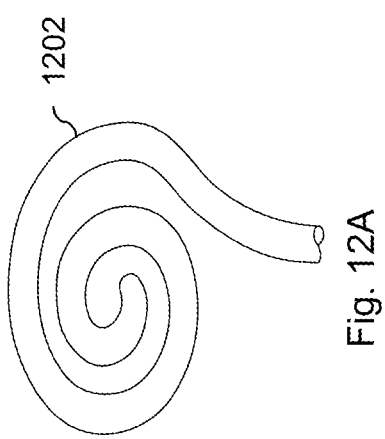
Figure 12C:
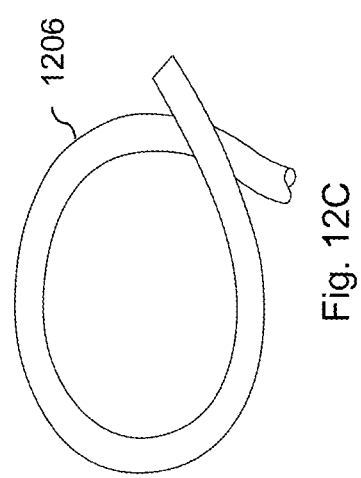

FIGS. 12A-12C depict enlarged views of various embodiments of a retention device, in accordance with an embodiment of the invention. In some embodiments, the retention device may be located proximate to a distal end portion of a medical device. In other embodiments, the retention device may be located proximate to a proximal end portion of the medical device. The retention device is formed by bending a portion that is proximate to the proximal/distal end portion of the elongate member into a substantially planar spiral configuration as depicted in FIGS. 12A-12C. The bending helps to retain the proximal/distal portion or the proximal/distal end portion of the medical device in place within the patient. In one embodiment, as shown in FIG. 12A, a retention device 1202 is formed by shaping the portion proximate to the proximal/distal portion into a planar spiral coil formed with a multiplicity of turns wound concentrically within the same plane. In another embodiment, as shown in FIG. 12B, a retention device 1204 is formed by shaping the portion proximate to the proximal/distal portion into a helical coil formed with at least one turn. In yet another embodiment, as shown in FIG. 12C, a retention device 1206 is the smallest configuration having slightly over one complete spiral turn of the portion proximate to the proximal/distal portion.

FIG. 13 is a schematic diagram of a medical device 1300 to be delivered into a patient's body, in accordance with an embodiment of the invention. The medical device 1300 may be a ureteral stent similar to the medical device 100 explained above in conjunction with FIG. 1. The medical device 1300 includes an elongate member 1302 having a proximal end portion 1304, a distal end portion 1306, and a medial portion 1308 that is disposed between the distal end portion 1306 and the proximal end portion 1304 of the elongate member 1302.

The medical device 1300 may further include a first expandable member 1310 and a second expandable member 1312, both being coupled to the elongate member 1302. In some embodiments, the first and second expandable members 1310 and 1312 may be balloons that may surround at least a portion of an external surface of the elongate member 1302. Referring to FIG. 13, the first expandable member 1310 is disposed at the distal end portion 1306 of the elongate member 1302 and the second expandable member 1312 is disposed at the proximal end portion 1304 of the elongate member 1302. The operator may deliver the medical device 1300 in the body of the patient such that the first expandable member 1310 is configured to be inserted into a kidney of the patient and the second expandable member 1312 is configured to be inserted into a urinary bladder of the patient. In some embodiments, the first expandable member 1310 may be configured in the expanded configuration to contact the kidney of the patient. Similarly, in some other embodiments, the second expandable member 1312 may be configured in the expanded configuration to contact the urinary bladder of the patient. These expandable members 1310 and 1312 thus help to retain the elongate member 1302 in place within the patient. The rest of the functionalities, arrangements, and implantation procedures of the medical device 1300 and its sub-elements are the same as that of the medical device 100.

Figure 14:
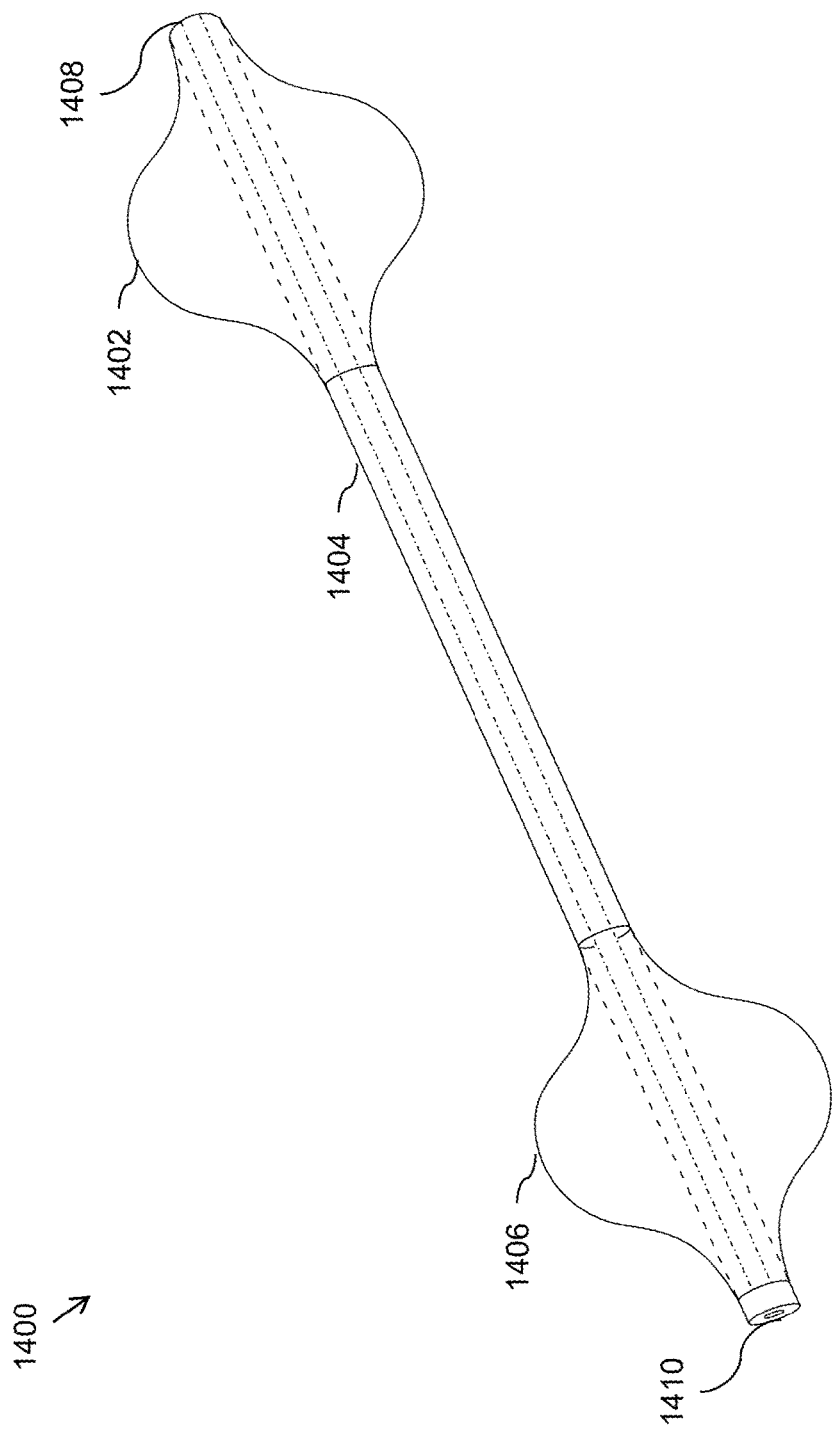
FIG. 14 is a perspective view of a medical device in an expanded configuration, in accordance with an embodiment of the invention.

FIG. 14 is a perspective view of a medical device 1400 in an expanded configuration, in accordance with an embodiment of the invention. The medical device 1400 includes a first expandable member 1402, in the expanded configuration, surrounding at least a portion of an elongate member 1404 of the medical device 1400. The medical device 1400 further includes a second expandable member 1406, in the expanded configuration, surrounding at least a portion of the elongate member 1404 of the medical device 1400. Referring to FIG. 14, the first expandable member 1402 is disposed at a distal end portion 1408 of the elongate member 1404 and the second expandable member 1406 is disposed at a proximal end portion 1410 of the elongate member 1404. The operator may deliver the medical device 1400 in the body of the patient such that the first expandable member 1404 is configured to be inserted into a renal pelvis of a kidney of the patient and the second expandable member 1406 is configured to be inserted into a urinary bladder of the patient. The rest of the functionalities, arrangements, and implantation procedures of the medical device 1400 and its sub-elements are the same as that of the medical device 200.

Figure 15:
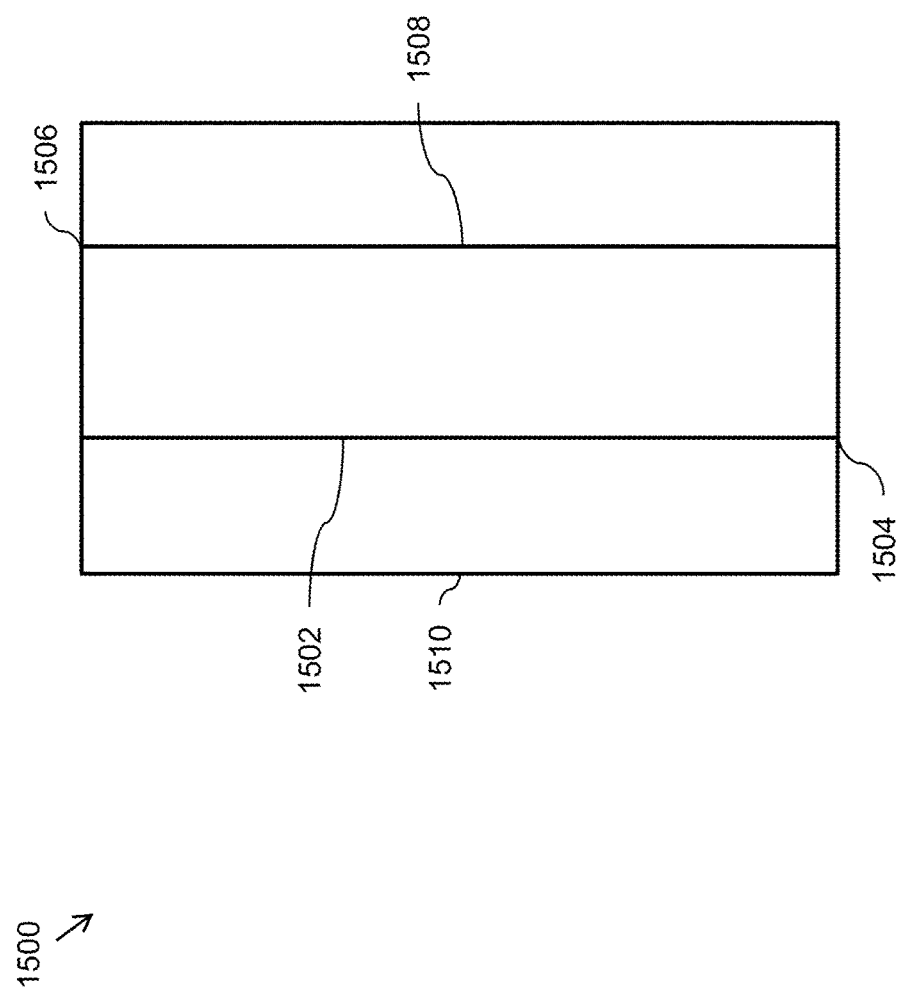
FIG. 15 is a schematic diagram of a medical device to be delivered into a patient's body, in accordance with an embodiment of the invention.

FIG. 15 is a schematic diagram of a medical device 1500 to be delivered into a patient's body, in accordance with an embodiment of the invention. The medical device 1500 may be a ureteral stent similar to the medical device 100 explained above in conjunction with FIG. 1. The medical device 1500 includes an elongate member 1502 having a proximal end portion 1504, a distal end portion 1506, and a medial portion 1508 that is disposed between the distal end portion 1506 and the proximal end portion 1504 of the elongate member 1502.

The medical device 1500 may further include an expandable member 1510 that is coupled to the elongate member 1502. In some embodiments, the expandable member 1510 may be a balloon that may surround at least a portion of an external surface of the elongate member 1502. Referring to FIG. 15, the expandable member 1510 extends from the proximal end portion 1504 of the elongate member 1502 to the distal end portion 1506 of the elongate member 1502. The operator may deliver the medical device 1500 in the body of the patient such that the expandable member 1510 is configured to be inserted into a urinary tract of the patient. The expandable member 1510 helps to retain the elongate member 1502 in place within the patient. The rest of the functionalities, arrangements, and implantation procedures of the medical device 1500 and its sub-elements are the same as that of the medical device 100.

Figure 16:
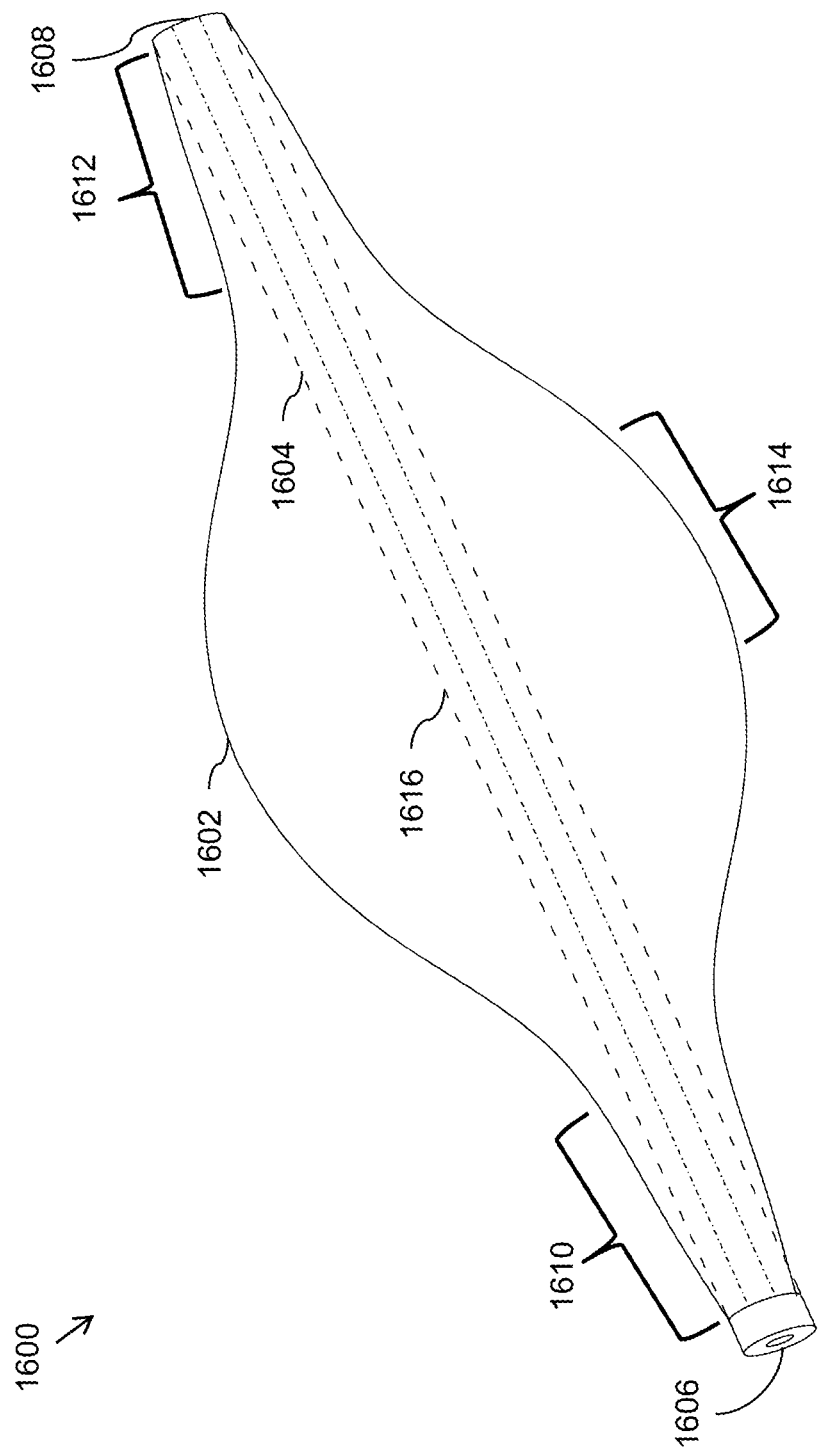
FIG. 16 is a perspective view of a medical device in an expanded configuration, in accordance with an embodiment of the invention.

FIG. 16 is a perspective view of a medical device 1600 in an expanded configuration, in accordance with an embodiment of the invention. The medical device 1600 includes an expandable member 1602, in the expanded configuration, surrounding an elongate member 1604 of the medical device 1600 completely. Referring to FIG. 16, the expandable member 1602 extends from a proximal end portion 1606 of the elongate member 1604 to a distal end portion 1608 of the elongate member 1604. The operator may deliver the medical device 1600 in the body of the patient such that the expandable member 1602 is configured to be inserted into a urinary tract of the patient. As illustrated in FIG. 16, a proximal portion 1610 of the expandable member 1602 may be disposed proximate to the proximal end portion 1606 of the elongate member 1604, a distal portion 1612 of the expandable member 1602 may be disposed proximate to the distal end portion 1608 of the elongate member 1604, and a medial portion 1614 of the expandable member 1602 may be disposed proximate to a medial portion 1616 of the elongate member 1604.

The expandable member 1602 may be configured in the expanded configuration to contact a ureter of the patient. In some embodiments, the expandable member 1602 may be configured in the expanded configuration such that the medial portion 1614 of the expandable member 1602 may contact the ureter of the patient and the distal portion 1612 of the expandable member 1602 may contact the kidney of the patient. In yet other embodiments, the expandable member 1602 may be configured in the expanded configuration such that the medial portion 1614 of the expandable member 1602 may contact the ureter of the patient and the proximal portion 1610 of the expandable member 1602 may contact a urinary bladder of the patient. In other embodiments, the expandable member 1602 may be configured in the expanded configuration such that the medial portion 1614 of the expandable member 1602 may contact the ureter of the patient, the proximal portion 1610 of the expandable member 1602 may contact the urinary bladder of the patient, and the distal portion 1612 of the expandable member 1602 may contact the kidney of the patient. The rest of the functionalities, arrangements, and implantation procedures of the medical device 1600 and its sub-elements are the same as that of the medical device 200.

Figure 17:
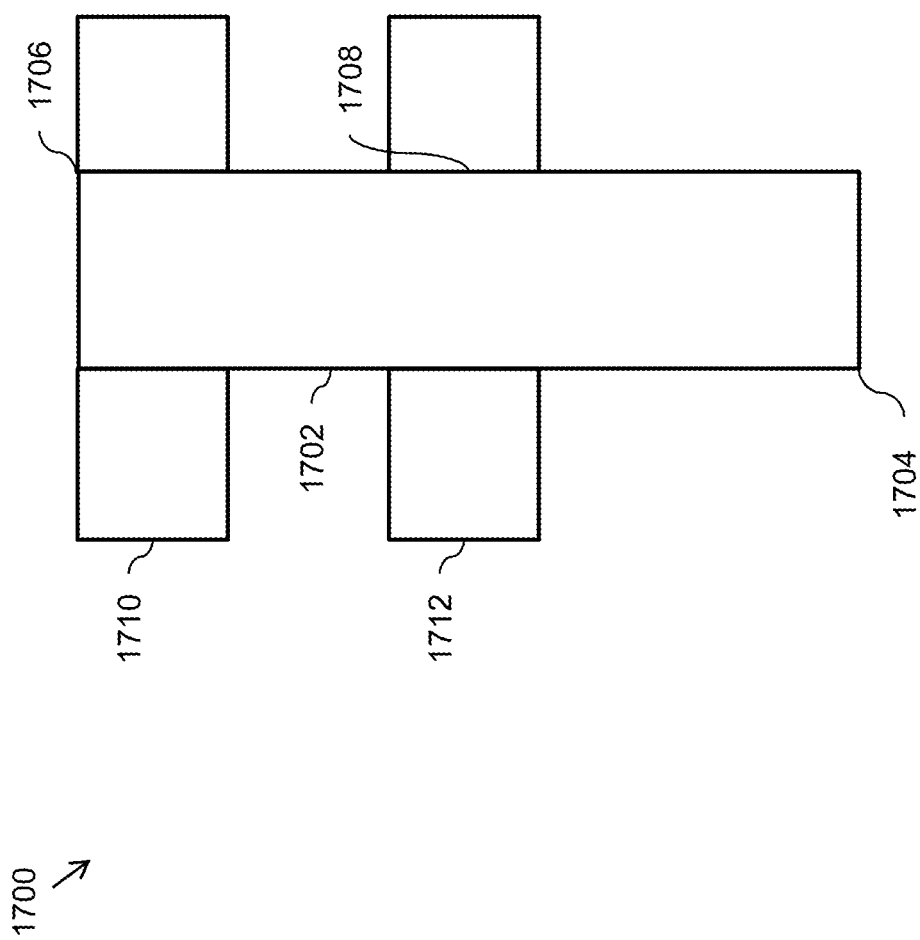
FIG. 17 is a schematic diagram of a medical device to be delivered into a patient's body, in accordance with an embodiment of the invention.

FIG. 17 is a schematic diagram of a medical device 1700 to be delivered into a patient's body, in accordance with an embodiment of the invention. The medical device 1700 may be a ureteral stent similar to the medical device 100 explained above in conjunction with FIG. 1. The medical device 1700 includes an elongate member 1702 having a proximal end portion 1704, a distal end portion 1706, and a medial portion 1708 that is disposed between the distal end portion 1706 and the proximal end portion 1704 of the elongate member 1702.

The medical device 1700 may further include a first expandable member 1710 and a second expandable member 1712, both being coupled to the elongate member 1702. In some embodiments, the first 1710 and the second 1712 expandable members may be balloons that may surround at least a portion of an external surface of the elongate member 1702. Referring to FIG. 17, the first expandable member 1710 is disposed at the distal end portion 1706 of the elongate member 1702 and the second expandable member 1712 is disposed at the medial portion 1708 of the elongate member 1702. The operator may deliver the medical device 1700 in the body of the patient such that the first expandable member 1710 is configured to be inserted into a kidney of the patient and the second expandable member 1712 is configured to be inserted into a ureter of the patient. In some embodiments, the first expandable member 1710 may be in the expanded configuration to contact the kidney of the patient. Similarly, in some other embodiments, the second expandable member 1712 may be in the expanded configuration to contact the ureter of the patient. These expandable members 1710 and 1712 thus help to retain the elongate member 1702 within the body of patient. The rest of the functionalities, arrangements, and implantation procedures of the medical device 1700 and its sub-elements are the same as that of the medical device 100.

The medical device 1700 may optionally have a proximal retention device similar to any of the proximal retention devices depicted in FIGS. 11 and 12A-12C. In some embodiments, the proximal retention device may be positioned proximate to the proximal end portion 1704 of the elongate member 1702.

Figure 18:
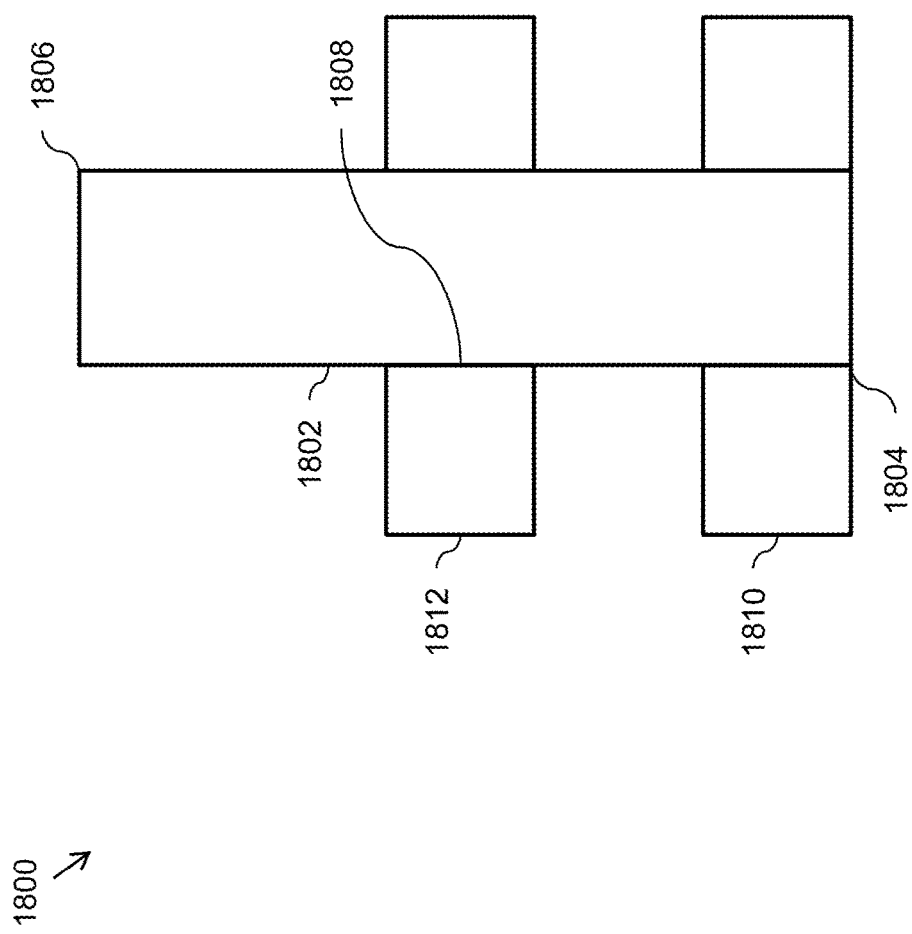
FIG. 18 is a schematic diagram of a medical device to be delivered into a patient's body, in accordance with another embodiment of the invention.

FIG. 18 is a schematic diagram of a medical device 1800 to be delivered into a patient's body, in accordance with another embodiment of the invention. The medical device 1800 may be a ureteral stent similar to the medical device 100 explained above in conjunction with FIG. 1. The medical device 1800 includes an elongate member 1802 having a proximal end portion 1804, a distal end portion 1806, and a medial portion 1808 that is disposed between the distal end portion 1806 and the proximal end portion 1804 of the elongate member 1802.

The medical device 1800 may further include a first expandable member 1810 and a second expandable member 1812, both being coupled to the elongate member 1802. In some embodiments, the first 1810 and the second 1812 expandable members may be balloons that may surround at least a portion of an external surface of the elongate member 1802. Referring to FIG. 18, the first expandable member 1810 is disposed at the proximal end portion 1804 of the elongate member 1802 and the second expandable member 1812 is disposed at the medial portion 1808 of the elongate member 1802. The operator may deliver the medical device 1800 in the body of the patient such that the first expandable member 1810 is configured to be inserted into a urinary bladder of the patient and the second expandable member 1812 is configured to be inserted into a ureter of the patient. In some embodiments, the first expandable member 1810 may be configured in the expanded configuration to contact the urinary bladder of the patient. Similarly, in some other embodiments, the second expandable member 1812 may be configured in the expanded configuration to contact the ureter of the patient. These expandable members 1810 and 1812 help to retain the elongate member 1802 in place within the patient. The rest of the functionalities, arrangements, and implantation procedures of the medical device 1800 and its sub-elements are the same as that of the medical device 100.

The medical device 1800 may optionally have a distal retention device similar to any of the distal retention devices depicted in FIGS. 3, 8, and 12A-12C. In some embodiments, the distal retention device may be positioned proximate to the distal end portion 1806 of the elongate member 1802.

Figure 19:
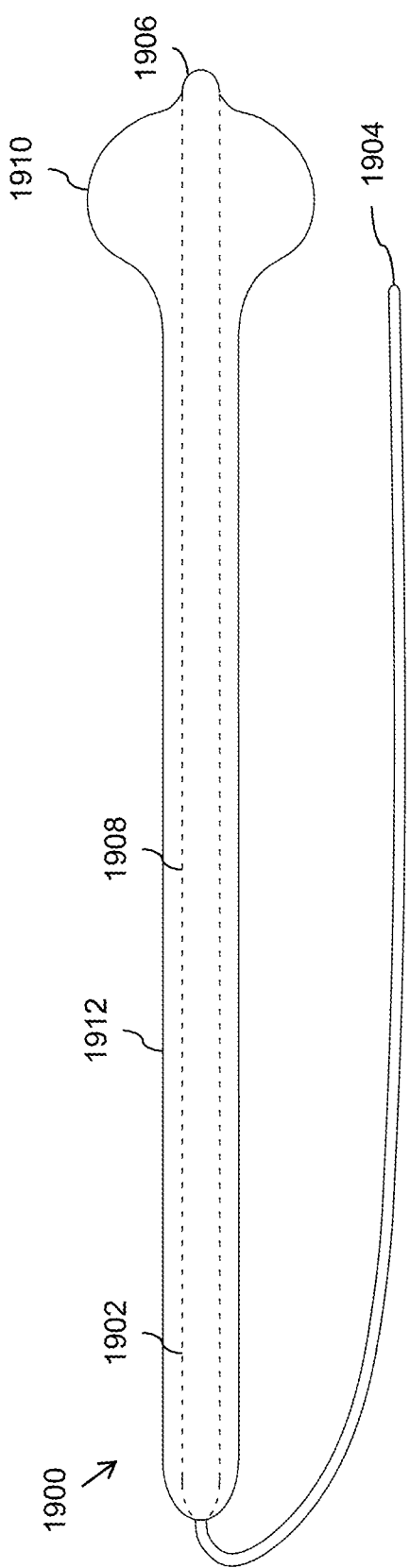
FIG. 19 is a perspective view of a medical device in an expanded configuration, in accordance with an embodiment of the invention.

FIG. 19 is a perspective view of a medical device 1900 in an expanded configuration, in accordance with an embodiment of the invention. The medical device 1900 includes an elongate member 1902 having a proximal end portion 1904, a distal end portion 1906, and a medial portion 1908 that is disposed between the distal end portion 1906 and the proximal end portion 1904 of the elongate member 1902.

The medical device 1900 further includes an expandable member 1910, in the expanded configuration, surrounding at least a portion of the elongate member 1902 of the medical device 1900. Referring to FIG. 19, the expandable member 1910 has two different shapes and sizes at the distal end portion 1906 and the medial portion 1908. A bigger portion (i.e., with larger diameter) of the expandable member 1910 is disposed at the distal end portion 1906 of the elongate member 1902. A smaller portion (i.e., with smaller diameter) of the expandable member 1910 is disposed at the medial portion 1908 of the elongate member 1902. In some embodiments, the smaller portion may be extended beyond the medial portion 1908 toward the proximal end portion 1904 of the elongate member 1902. In an embodiment, the diameter of the bigger portion is kept larger by filling more medium in the bigger portion as compared to that filled in the smaller portion of the expandable member 1910.

In an embodiment, the operator may deliver the medical device 1900 in the body of the patient using a pusher catheter such that the bigger portion of the expandable member 1910 is configured to be disposed into a renal pelvis of a kidney of the patient, and the smaller portion of the expandable member 1912 is configured to be disposed into a ureter of the patient to help retain the elongate member 1902 in place within the patient. Alternatively, in another embodiment, the bigger portion may be disposed in the ureter close to the kidney of the patient. In some embodiments where the medical device 1900 is placed within the patient, the expandable member 1910 may be inflated for dilatation and then deflated for comfort. In one embodiment, the proximal end portion 1904 of the elongate member 1902 may extend to a location out of the body of the patient and may be used to inflate or deflate the expandable member 1910 (for example, an inflation lumen may be defined by the portion of the device between the proximal end portion 1904 and the medial portion). In another embodiment, at least a portion of the proximal end portion 1904 is close to the body of the patient and at least another portion of the proximal end portion 1904 may be disposed in the urinary bladder of the patient. The rest of the functionalities, arrangements, and implantation procedures of the medical device 1900 and its sub-elements are the same as that of the medical device 200.

Alternatively, in another embodiment, the smaller portion and the bigger portion of the expandable member 1910 may be two different expandable members that may be separately inflated and deflated.

Figure 20:
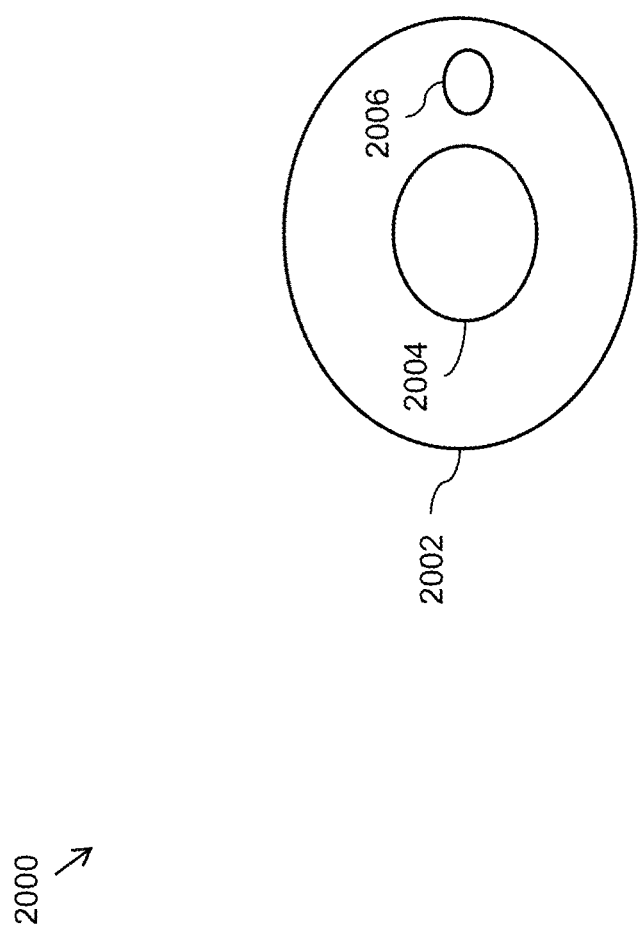
FIG. 20 illustrates an end view of a medical device with two lumens, in accordance with an embodiment of the invention.

As described earlier in conjunction with FIG. 2, the elongate member 202 defines the lumen 212 to permit drainage of urine from a kidney of the patient directly into a urinary bladder of the patient. An elongate member may define another lumen for fluid communication with an expandable member. FIG. 20 illustrates an end view of a medical device 2000 with two lumens, in accordance with an embodiment of the invention. The medical device 2000 may be a ureteral stent that includes an elongate member 2002 defining a first lumen 2004 and a second lumen 2006. The first lumen 2004 may extend between a proximal end portion and a distal end portion along the longitude of the elongate member 2002. In some embodiments, the first lumen 2004 of the elongate member 2002 may be disposed through a center of an expandable member (not shown in FIG. 20) coupled to the elongate member 2002 so as to permit drainage of urine from a kidney of a patient directly into a urinary bladder of the patient. Since the first lumen 2004 is used for drainage of urine, it is hereinafter interchangeably referred to as the drainage lumen 2004.

In some embodiments, the second lumen 2006 may be in fluid communication with an interior or a cavity of the expandable member that is configured to be inflated with a fluid conveyed to the expandable member via the second lumen 2006. Since the second lumen 2006 facilitates fluid communication used for inflation of the expandable member, the second lumen 2006 is hereinafter interchangeably referred to as the inflation lumen 2006. In certain embodiments, a valve may be disposed within the second lumen 2006 to permit fluid to flow through the second lumen 2006 towards the expandable member. Further, in embodiments having two expandable members, the elongate member 2002 may define a third lumen (not shown in the FIG. 20) for fluid communication with a cavity of the other expandable member. In this case, the second lumen 2006 will be used for fluid communication with the cavity of the first expandable member.

Figure 21A:
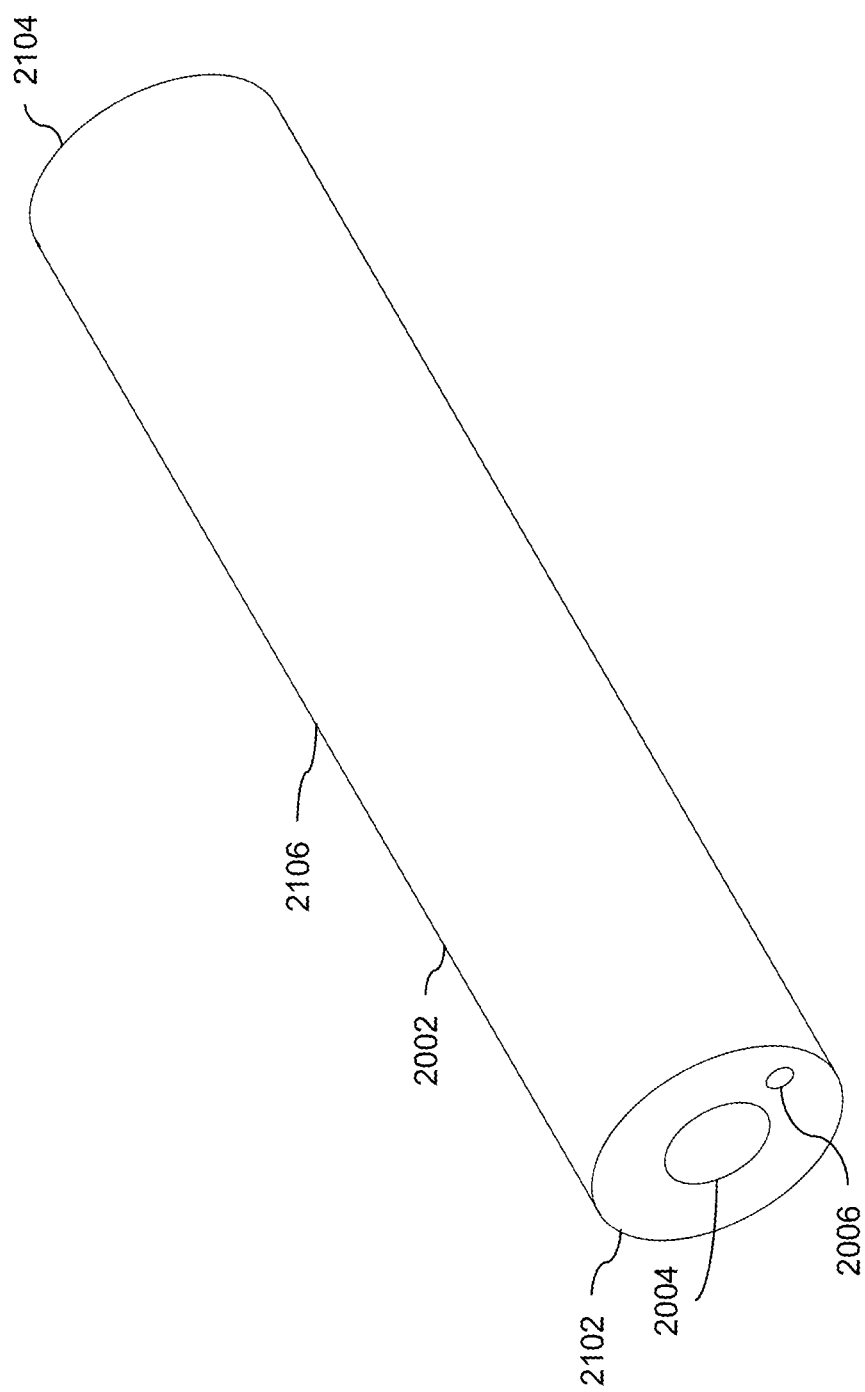
FIGS. 21A and 21B illustrate perspective views of medical devices.
Figure 21B:
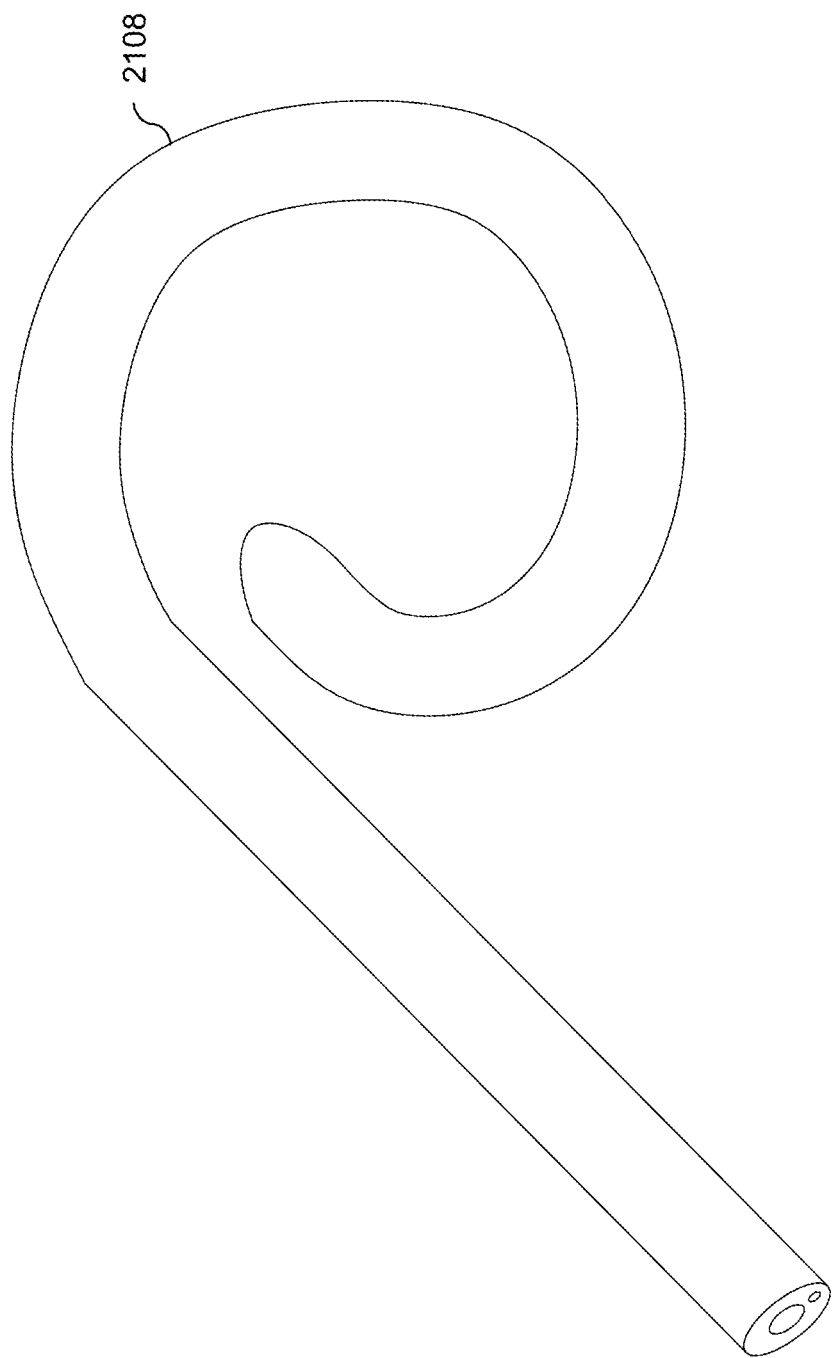

FIGS. 21A and 21B illustrate perspective views of the medical device 2000. The elongate member 2002 of the medical device 2000 has a proximal end portion 2102, a distal end portion 2104, and a medial portion 2106 that may be disposed at a medial location of the elongate member 2002 between the distal end portion 2104 and the proximal end portion 2102. The elongate member 2002 extends longitudinally between the distal end portion 2104 and the proximal end portion 2104. One or both ends of the medical device 2000 may be coiled in a pigtail spiral, substantially helical, or J-shape to prevent the upward and/or downward migration of the medical device 2000 in a lumen of the medical device 2000 due to, for example, the day-to-day physical activity of the patient. As illustrated in FIG. 21B, the medical device 2000 may include a J-shaped proximal retention device 2108 that is disposed proximate to the distal end portion 2104 of the elongate member 2002. The proximal retention device 2108 may be positioned in a kidney of the patient to help prevent medical device migration downward toward the bladder. Likewise, a proximal retention device in a bladder portion of the patient may help retain the medical device within the bladder and prevent medical device migration upward toward the kidney. In other embodiments, one or both ends of the elongate member 2002 may include one or more expandable members. In yet other embodiments, the medial portion 2106 of the elongate member 2002 and/or one or both ends of the elongate member 2002 may include one or more expandable members.

The size and shape of the elongate member 2002 and the proximal retention device 2108 as illustrated in FIGS. 21A and 21B are merely exemplary, and various other shapes and sizes are possible without limiting the spirit and scope of the invention.

There are two conventional techniques of placing the medical devices. In the first technique, a guidewire of sufficient stiffness and maneuverability is placed into the body of the patient through the urinary tract up to the kidney. Once the guidewire has been passed into the body of the patient, the medical device is placed into the ureter over the guidewire using a pusher catheter acting on a proximal end of the medical device. The second technique omits the prior step of placing the guidewire and may be used where no large obstruction is present. FIG. 22 illustrates a perspective view of a medical device 2200 in a pre-deployed or collapsed configuration using this second technique, in accordance with an embodiment of the invention. In this technique, the medical device 2200 having an elongate member (not shown in FIG. 22) and an expandable member 2202 coupled to the elongate member is deployed over a guidewire 2204. The expandable member 2202 is in collapsed configuration in this pre-deployment embodiment to allow the medical device 2200 to be easily inserted into the body of the patient. As described above, the expandable member 2202 may be positioned at a medial portion of the elongate member of the medical device 2200. In other embodiments, the expandable member 2202 may be extended to a distal end portion or a proximal end portion of the elongate member. In yet other embodiments, the expandable member 2202 may be disposed over an entire length of the elongate member. In other embodiments, the expandable member 2202 and an additional expandable member similar to the expandable member 2202 may be disposed over any two of the distal end portion, the proximal end portion, and the medial portion of the elongate member.

As illustrated in FIG. 22, the medical device 2200 may be placed over the guidewire 2204 using an insertion device 2206 that is positioned proximate to a proximal portion 2208 of the guidewire 2204. This placement facilitates in engaging the medical device 2200 within the patient. In an embodiment, the medical device 2200 is engaged by passing the insertion device 2206 through a urinary bladder of the patient. In another embodiment, the medical device 2200 is engaged by inserting at least a portion of the insertion device 2206 into a ureter of the patient. In FIG. 22, the insertion device 2206 is disposed over the guidewire 2204. In some embodiments, the insertion device 2206 may be a pusher tube or a pusher catheter that is placed behind the medical device 2200 to push the medical device 2200 in place within the patient. In some embodiments, the operator may push the insertion device 2206 on a proximal end portion of the medical device 2200 in order to insert the medical device 2200 into the body of the patient. In other embodiments, the operator may remove the medical device from the body of the patient by pulling the insertion device 2206 away from the patient's body. Both the medical device 2200 and the insertion device 2206 are dimensioned to fit the anatomical requirements of each application within the body of the patient.

Figure 23:
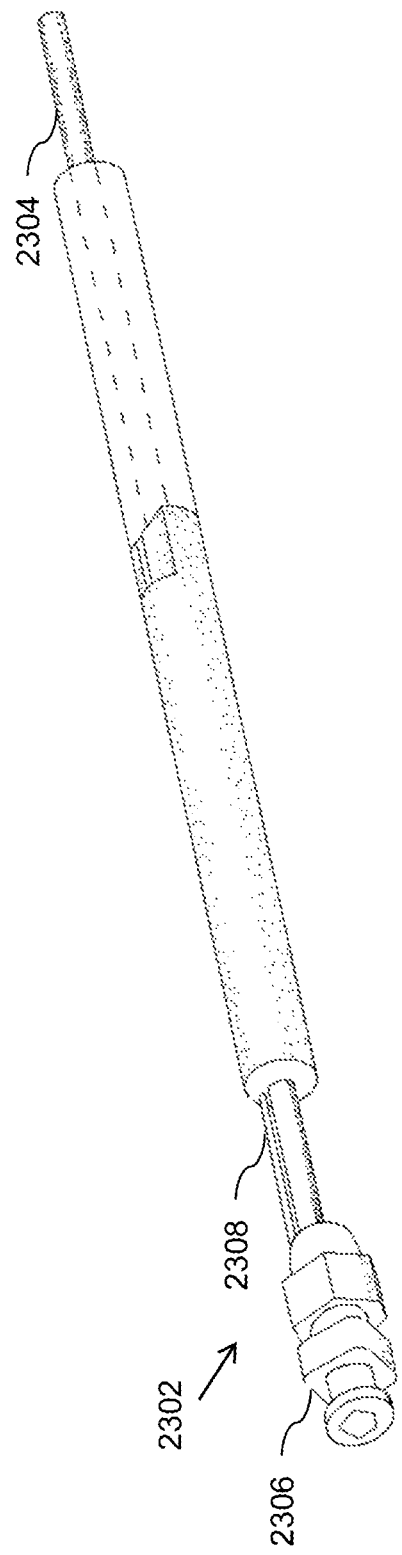
FIG. 23 illustrates a perspective view of an insertion device disposed over a guidewire, in accordance with an embodiment of the invention.

FIG. 23 illustrates a perspective view of an insertion device 2302 over a guidewire 2304, in accordance with an embodiment of the invention. The insertion device 2302 includes a luer fitting 2306 that is used to provide a secure seal appropriate for gas and fluid connections in medical applications. The insertion device 2302 defines a filler tube 2308 through which a medium such as liquid saline is introduced into an expandable member (such as the expandable member 2202) to inflate that expandable member. The filler tube acts as a lumen through which the fluid is passed for inflation and hence hereinafter interchangeably referred to as an inflation lumen of an insertion device. In other embodiments, the insertion device 2302 may define an additional filler tube for inflation of each additional expandable member. For example, in case two expandable members are used, the insertion device 2302 will define two filler tubes; each facilitate in passage of the respective expandable member. In some embodiments, at least a portion of the insertion device 2302 may extend outside the body of the patient. For example, the luer fitting 2306 and at least a portion of the filler tube 2308 may extend outside the body, while the medical device is inserted inside the body.

Figure 24:
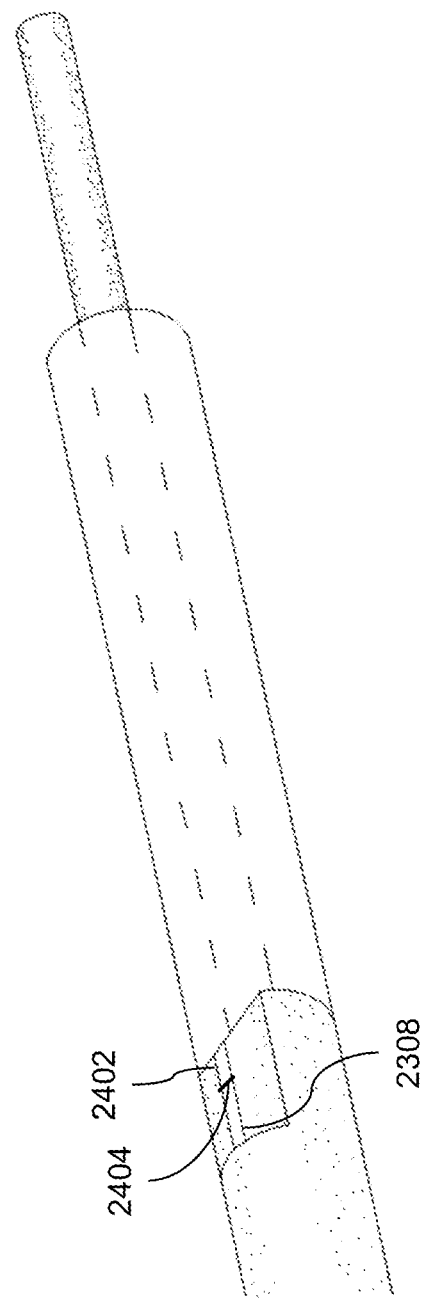
FIG. 24 illustrates an enlarged view of a portion of the insertion device of FIG. 23, in accordance with an embodiment of the invention.

FIG. 24 illustrates an enlarged view of a portion of the insertion device 2302, in accordance with an embodiment of the invention. This embodiment defines an interface between the filler tube 2308 and a valve 2402. In one embodiment, the valve 2402 may be a unidirectional check valve that allows fluid to flow in only one direction, i.e., toward the expandable member of the medical device (not shown in FIG. 24). Unidirectional flow of fluid toward the expandable member will facilitate in the placement of the expandable member in the expanded configuration. In another embodiment, the valve 2402 may be a bidirectional check valve that allows fluid to flow in both directions, thereby facilitating the placement of the expandable member in the expanded and collapsed configurations. In some embodiments, the valve 2402 may be disposed at a proximal end portion of an elongate member of the medical device to which the insertion device 2302 is connected. In certain embodiments, a valve inlet 2404 of the valve 2404 may open when a sufficient fluid pressure is exerted at the valve inlet 2404. In various embodiments, the valve inlet 2404 opens to facilitate communication of fluid to the expandable member once the medical device is already inserted into the body of the patient and the valve inlet 2404 closes once the fluid in the expandable member is filled to a desired quantity and the medical device is engaged within the body of the patient. In certain embodiments when the valve 2402 is bidirectional, the valve inlet 2404 may open to allow the fluid to be removed from the expandable member. The operator may do so when the medical device is to be removed from the body of the patient.

FIG. 25 is a front view of a medical device 2502 and an insertion device 2504, in accordance with an embodiment of the invention. The medical device 2502 may be a ureteral stent suitable for use with the insertion device 2504 for implantation within a ureter of a patient. The medical device 2502 includes an elongate member 2506 having a proximal end portion 2508, a distal end portion 2510, and a medial portion 2512 that is disposed between the distal end portion 2510 and the proximal end portion 2508 of the elongate member 2506.

The medical device 2502 may further include an expandable member 2514 that may be coupled to the elongate member 2506. In some embodiments, the expandable member 2514 may be a balloon that may surround at least a portion of an external surface of the elongate member 2506. In other embodiments, the expandable member 2514 may be any other expandable material that has the property to expand and collapse. Referring to FIG. 25, the expandable member 2514 is positioned at the medial portion 2512 of the elongate member 2506.

The elongate member 2506 defines a lumen 2516 that extends between the proximal end portion 2508 and the distal end portion 2510 along the longitude of the elongate member 2506. In some embodiments, the lumen 2516 of the elongate member 2506 may be disposed through a center of the expandable member 2514 to permit drainage of urine from a kidney of the patient directly into a urinary bladder of the patient. In some embodiments, this center of the expandable member 2514 is the cavity of the expandable member 2514.

In some embodiments, one or both ends of the elongate member 2506 may be coiled in a spiral shape or J-shape or substantially helical shape to further prevent the upward and/or downward migration of the medical device 2502 in the ureter due to, for example, the day-to-day physical activity of the patient. As shown in FIG. 25, a J-shaped distal retention device 2518 is disposed proximate to the distal end portion 2510 and is configured to be disposed in the kidney of the patient once the medical device 2502 is inserted into the body of the patient. The distal retention device 2518 may help retain the medical device 2502 within a renal pelvis of the kidney and prevent the medical device 2502 migration down the ureter. Likewise, a proximal retention device may optionally be disposed proximate to the proximal end portion 2508 and may be configured to be disposed in a urinary bladder of the patient to help prevent the medical device 2502 migration upward toward the kidney. In other embodiments, one or both ends of the medical device 2502 may include one or more expandable members similar to the expandable member 2514 so as to prevent the medical device 2502 migration.

The medical device 2502 further includes a valve 2520 to facilitate in the placement of the expandable member 2514 in the expanded and collapsed configurations. In an embodiment, the valve 2520 may be a bidirectional check valve that allows fluid to flow in both directions, thereby facilitating the placement of the expandable member 2514 in the expanded and collapsed configurations. In some embodiments as shown in FIG. 25, the valve 2520 is disposed on the expandable member 2514. In other embodiments, the valve 2520 may be disposed on the elongate member 2504. In one embodiment, the valve 2520 includes a valve inlet 2522 for inflation and deflation of the expandable member 2514 with a suitable biocompatible fluid such as biocompatible gas or liquid.

Referring to FIG. 25, the insertion device 2504 has a sidewall 2524 that defines a central lumen 2526 and an inflation lumen 2528 of the insertion device 2504. The central lumen 2526 may permit urine drainage. The inflation lumen 2528 may permit delivery of the fluid into the expandable member 2514. Further, a port 2530 is disposed at one end of the inflation lumen 2528 and engages the valve inlet 2522 for delivery of the fluid into the expandable member 2514. The valve inlet 2522 opens when engaged by the port 2530 of the insertion device 2504 and the valve 2520 will close when the port 2530 is disengaged from the valve inlet 2522.

The expandable member 2514 may be filled via the inflation lumen 2528 of the insertion device 2504 with a liquid pharmaceutical such as, but not limited to, an anesthetic, an antispasmodic agent, an anti-cholinergic agent, a chemotherapeutic agent, or an agent for transfection of genes. The pharmaceutical agent contained within the expandable member 2514 may be released into the urinary bladder through various known means such as, but not limited to, a small orifice 2532 perforated through the expandable member 2514, or controlled release through the valve inlet 2522 of the valve 2520. In another embodiment, the expandable member 2514 may contain a plurality of perforated orifices to release the pharmaceutical agent into the urinary bladder.

In some embodiments, the valve inlet 2522 may open by pulling a retrieval suture 2534 to deflate the expandable member 2514 and allow removal of the medical device 2502 from the body of the patient. In one embodiment, the retrieval suture 2534 may be coupled to the elongate member 2506. In another embodiment as illustrated in FIG. 25, the retrieval suture 2534 is coupled to the expandable member 2514. In some embodiments, the retrieval suture 2534 may remove a plug (not shown in FIG. 25) in the expandable member 2514 to deflate the expandable member 2514. In some other embodiments, a needle device or a syringe may be used to deflate the expandable member 2514. In yet another embodiment, a laser-type device may be inserted within the body of the patient to provide energy to the expandable member 2514 to inflate or deflate the expandable member 2514. Using any of these devices, the operator may deflate the expandable member 2514 such that the diameter of the expandable member 2514 is restored to substantially the same diameter as the diameter of the medial portion 2510 of the elongate member 2506 of the medical device 2502.

The configuration of the medical device 2502 and the insertion device 2504 may be delivered into the body of the patient. In some embodiments, the insertion device 2504 may be used to deliver the medical device 2502 through a cytoscope over a guidewire (not shown in FIG. 25) and into the urinary tract. In certain other embodiments, a medical device may be introduced endoscopically without the use of the insertion device 2504. Once inserted into the ureter of the patient, the expandable member 2514 may be inflated to contact the ureter to help retain the elongate member 2506 in place within the patient. The operator may then remove the medical device 2502 from the body of the patient. In some embodiments, the retrieval suture 2534 may be used for retrieval of the medical device 2502 from the urinary tract of the patient. In other embodiments, a proximal retention device may facilitate the operator in the removal of the medical device 2502.

The present invention has been described in conjunction with a medical device (such as 100, 200, 300, 600, 700, 800, 900, 1000, 1100, 1300, 1400, 1500, 1600, 1700, 1800, 1900, 2000, 2200, or 2502). However, various other types of medical devices (including conventional devices), slings, support members, suture bundles, pull rods, sleeves, other bolstering materials, and the like may be equally used to be delivered into the patient's body with the use of the teachings of the invention.

In some embodiments, an apparatus includes an elongate member having a distal end portion, a proximal end portion, and a medial portion disposed between the distal end portion and the proximal end portion. The medial portion is configured to be disposed in a ureter of a patient. An expandable member is coupled to the elongate member. The expandable member has an expanded configuration and a collapsed configuration. The expandable member is configured to be inserted into the ureter of the patient. The expandable member is configured to contact the ureter to help retain the elongate member in place within the patient.

In some embodiments, the expandable member includes a balloon defining a cavity. In some embodiments, the expandable member is configured to be inserted into the ureter of the patient in the collapsed configuration. In some embodiments, the expandable member is configured to contact the ureter of the patient when the expandable member is in the expanded configuration. In some embodiments, the expandable member is positioned at the medial portion of the elongate member. In some embodiments, the expandable member is disposed at the distal end portion of the elongate member. In some embodiments, the expandable member is disposed at the proximal end portion of the elongate member. In some embodiments, the expandable member extends from the proximal end portion of the elongate member to the distal end portion of the elongate member. In some embodiments, the distal end portion of the elongate member is configured to be disposed in a kidney of the patient.

In some embodiments, the apparatus includes a distal retention device disposed proximate the distal end portion of the elongate member. The distal retention device is configured to help retain the distal end portion of the elongate member in a kidney of the patient. In some embodiments, the expandable member is a first expandable member and the distal retention device includes one of a spiral, a substantially helical coil, and a second expandable member. In some embodiments, the proximal end portion of the elongate member is configured to be disposed in a urinary bladder of the patient.

In some embodiments, the apparatus includes a proximal retention device disposed proximate the proximal end portion of the elongate member. The proximal retention device is configured to help retain the proximal end portion of the elongate member in a urinary bladder of the patient. In some embodiments, the expandable member is a first expandable member. The proximal retention device includes one of a spiral, a substantially helical coil, and a second expandable member.

In some embodiments, a system includes a medical device and an insertion member. The medical device has an elongate member and an expandable member. The elongate member has a distal end portion, a proximal end portion, and a medial portion disposed between the distal end portion and the proximal end portion. The medial portion is configured to be disposed in a ureter of a patient. The expandable member is coupled to the elongate member. The expandable member has an expanded configuration and a collapsed configuration. The expandable member is configured to be inserted into the ureter of the patient and the expandable member is configured to contact the ureter to help retain the elongate member in place within the patient. The insertion device has a side wall. The side wall defines a central lumen and an inflation lumen. The insertion device is configured to engage the medical device within the patient.

In some embodiments, the medical device includes a valve configured to facilitate the placement of the expandable member in the expanded and collapsed configurations. In some embodiments, the medical device includes a retrieval suture configured to place the expandable member in the collapsed configuration.

In some embodiments, the system includes a needle device for deflating the expandable member. In some embodiments, the expandable member is configured to be inserted into the ureter of the patient in the collapsed configuration. In some embodiments, the expandable member is configured to contact the ureter of the patient when the expandable member is in the expanded configuration. In some embodiments, the distal end portion of the elongate member is configured to be disposed in a kidney of the patient.

In some embodiments, the system includes a distal retention device disposed proximate the distal end portion of the elongate member. The distal retention device is configured to help retain the distal end portion of the elongate member in a kidney of the patient. In some embodiments, the expandable member is a first expandable member, the distal retention device includes one of a spiral, a substantially helical coil, and a second expandable member. In some embodiments, the proximal end portion of the elongate member is configured to be disposed in a urinary bladder of the patient.

In some embodiments, the system includes a proximal retention device disposed proximate the proximal end portion of the elongate member. The proximal retention device is configured to help retain the proximal end portion of the elongate member in a urinary bladder of the patient. In some embodiments, the expandable member is a first expandable member. The proximal retention device includes one of a spiral, a substantially helical coil, and a second expandable member.

In some embodiments, a method for implanting a medical device into a body of a patient includes (1) inserting the medical device into a urinary tract of the patient, the medical device including an elongate member and an expandable member coupled to the elongate member, the elongate member having a distal end portion, a proximal end portion, and a medial portion disposed between the distal end portion and the proximal end portion, the medial portion being configured to be disposed in a ureter of the patient; and (2) expanding the expandable member such that at least a portion of the expandable member contacts the ureter to help retain the elongate member in place within the patient.

In some embodiments, the method includes placing a proximal retention device of the medical device disposed proximate the proximal end portion of the elongate member in a urinary bladder of the patient. In some embodiments, the method includes placing a distal retention device of the medical device disposed proximate the distal end portion of the elongate member in a kidney of the patient. In some embodiments, the inserting includes inserting the expandable member into the ureter of the patient in a collapsed configuration. In some embodiments, the expanding includes contacting the ureter of the patient when the expandable member is in an expanded configuration. In some embodiments, the expandable member is disposed at the medial portion of the elongate member. In some embodiments, the expandable member is disposed at the distal end portion of the elongate member. In some embodiments, the expandable member is disposed at the proximal end portion of the elongate member. In some embodiments, the expandable member extends from the proximal end portion of the elongate member to the distal end portion of the elongate member.

In some embodiments, the method includes placing a valve disposed on the medical device into the body of the patient to facilitate the placement of the expandable member in the expanded and collapsed configurations. In some embodiments, the medical device includes a retrieval suture configured to place the expandable member in a collapsed configuration.

In some embodiments, the method includes deflating the expandable member, and removing the medical device from the body of the patient. In some embodiments, the method includes engaging the medical device with an insertion device within the body of the patient, the insertion device defining a central lumen and an inflation lumen. In some embodiments, the engaging includes passing the insertion device through a urinary bladder of the patient. In some embodiments, the engaging includes inserting at least a portion of the insertion device into the ureter.

The present invention has been disclosed and described in terms of the treatment of ureteral obstruction or injury, or to protect the integrity of a ureter in various surgical operations. The present invention may find applications in the treatment of other bodily structures or lumen.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. An apparatus, comprising:
   an elongate member having a distal end portion, a proximal end portion, and a medial portion disposed between the distal end portion and the proximal end portion, the medial portion being configured to be disposed in a ureter of a patient, the elongate member defining a lumen extending through the distal end portion, the proximal end portion, and the medial portion;

an expandable member coupled to the distal end portion of the elongate member, the expandable member having an expanded configuration and a collapsed configuration and a valve disposed on the expandable member, the expandable member being configured to be inserted into the kidney of the patient and the expandable member being configured to contact the kidney to help retain the elongate member in place within the patient;

a guidewire configured to be inserted into the lumen of the elongate member; and an insertion device configured to be disposed over a portion of the guidewire, the insertion device including a fitting configured to provide a secure seal for fluid connections, the insertion device defining a filler tube extending from the fitting, the filler tube configured to engage the valve, while the expandable member is within the patient, to introduce fluid into the expandable member to inflate the expandable member within the kidney.

2. The apparatus of claim 1, wherein the expandable member includes a balloon defining a cavity; and
wherein the filler tube is configured to introduce the fluid through the valve.

3. The apparatus of claim 1, wherein the expandable member is configured to be inserted into the kidney of the patient in the collapsed configuration.

4. The apparatus of claim 1, wherein the expandable member is configured to contact the kidney of the patient when the expandable member is in the expanded configuration.

5. The apparatus of claim 1, wherein the distal end portion of the elongate member is configured to be disposed in a kidney of the patient.

6. The apparatus of claim 1, wherein the proximal end portion of the elongate member is configured to be disposed in a urinary bladder of the patient.

7. The apparatus of claim 1, further comprising:
a proximal retention device disposed proximate the proximal end portion of the elongate member, the proximal retention device being configured to help retain the proximal end portion of the elongate member in a urinary bladder of the patient.

8. The apparatus of claim 7, wherein the proximal retention device includes one of a spiral and a substantially helical coil.

9. An apparatus, comprising:
an elongate member having a distal end portion, a proximal end portion, and a medial portion disposed between the distal end portion and the proximal end portion, the medial portion being configured to be disposed in a ureter of a patient, the distal end portion being configured to be disposed in a kidney of the patient, the elongate member defining a lumen extending through the distal end portion, the proximal end portion, and the medial portion;

an expandable member coupled to the proximal portion of the elongate member, the expandable member having an expanded configuration and a collapsed configuration and a valve disposed on the expandable member, the expandable member being configured to be inserted into the bladder of the patient and the expandable member being configured to contact the bladder to help retain the elongate member in place within the patient;

a guidewire configured to be inserted into a lumen of the elongate member; and an insertion device configured to be disposed over a portion of the guidewire, the insertion device including a fitting configured to provide a secure seal for fluid connections, the insertion device defining a filler tube extending from the fitting, the filler tube configured to engage the valve, while the expandable member is within the patient, to introduce fluid into the expandable member to inflate the expandable member within the bladder.

10. The apparatus of claim 9, wherein the expandable member includes a balloon defining a cavity; and
wherein the filler tube is configured to introduce the fluid through the valve.

11. The apparatus of claim 9, wherein the expandable member is configured to be inserted into the urinary bladder of the patient in the collapsed configuration.

12. A system comprising:
an elongate member having a distal end portion, a proximal end portion, and a medial portion disposed between the distal end portion and the proximal end portion, the proximal end portion configured to be disposed in a bladder of the patient, the distal end portion configured to be disposed in a kidney of the patient, the medial portion being configured to be disposed in a ureter of the patient;

a first expandable member coupled to the distal end portion of the elongate member, the first expandable member configured to be disposed in a kidney of a patient, the first expandable member having an expanded configuration and a collapsed configuration and a valve disposed on the first expandable member;

a second expandable member coupled to the proximal end portion of the elongate member, the second expandable member configured to be disposed in a bladder of the patient, the second expandable member having an expanded configuration and a collapsed configuration and a valve disposed on the second expandable member;

a guidewire configured to be inserted into a lumen of the elongate member; and an insertion device configured to be disposed over a portion of the guidewire, the insertion device including a luer fitting configured to provide a secure seal for fluid connections, the insertion device defining two filler tubes, each filler tube configured to engage the valve of a respective expandable member, while the respective expandable member is within the patient, and to introduce fluid into the respective expandable member.

13. The system of claim 12, wherein the first expandable member is a balloon that surrounds the distal end portion of the elongate member, and the second expandable member is a balloon that surrounds the proximal end portion of the elongate member; and
wherein each filler tube is configured to introduce the fluid through the valve of the balloon of the respective first expandable member and the second expandable member.

14. The apparatus of claim 9, wherein the expandable member is configured to contact the bladder of the patient when the expandable member is in the expanded configuration.

15. The apparatus of claim 9, wherein the proximal end portion of the elongate member is configured to be disposed in the bladder of the patient.

16. The apparatus of claim 9, further comprising:
a distal retention device disposed proximate the distal end portion of the elongate member, the distal retention device being configured to help retain the distal end portion of the elongate member in the kidney of the patient.

17. The apparatus of claim 16, wherein the distal retention device includes one of a spiral and a substantially helical coil.

* * * * *